US012133746B2

(12) United States Patent
Seybold et al.

(10) Patent No.: US 12,133,746 B2
(45) Date of Patent: Nov. 5, 2024

(54) SYSTEM AND APPARATUS FOR ASYNCHRONOUS TOTAL BODY IMAGING WITH SYNCHRONOUS LIVE FEED VIDEO CONSULTATION

(71) Applicant: Techara LLC, Concord, NH (US)

(72) Inventors: Karleen Seybold, Concord, NH (US); Nathaniel Santana, Tucson, AZ (US)

(73) Assignee: Techara LLC, York, ME (US)

( * ) Notice: Subject to any disclaimer, the term of this patent is extended or adjusted under 35 U.S.C. 154(b) by 582 days.

(21) Appl. No.: 17/385,133

(22) Filed: Jul. 26, 2021

(65) Prior Publication Data

US 2022/0151571 A1 May 19, 2022

Related U.S. Application Data

(60) Provisional application No. 63/056,223, filed on Jul. 24, 2020.

(51) Int. Cl.
*A61B 5/00* (2006.01)
*E04H 1/12* (2006.01)
(Continued)

(52) U.S. Cl.
CPC .......... *A61B 5/7465* (2013.01); *A61B 5/0046* (2013.01); *A61B 5/0077* (2013.01); *A61B 5/742* (2013.01); *E04H 1/1205* (2013.01); *G16H 30/20* (2018.01); *G16H 80/00* (2018.01); *H04L 65/403* (2013.01); *H04L 67/12* (2013.01); *A61B 2560/0431* (2013.01)

(58) Field of Classification Search
CPC .......... A61B 5/7465; A61B 2560/0431; A61B 5/0046; A61B 5/0077; A61B 5/742; E04H 1/1205; G16H 30/20; G16H 80/00; H04L 65/403; H04L 67/12
See application file for complete search history.

(56) References Cited

U.S. PATENT DOCUMENTS

| 2007/0079573 A1* | 4/2007 | Sarine | E04B 1/34305 52/592.1 |
| 2013/0173287 A1* | 7/2013 | Cashman | H04N 7/141 705/2 |

(Continued)

FOREIGN PATENT DOCUMENTS

WO WO-2016154147 A1 * 9/2016 ........... A61B 5/0077

Primary Examiner — Jordan L Jackson
(74) Attorney, Agent, or Firm — Zeman-Mullen & Ford, LLP

(57) ABSTRACT

A system for patient body imaging with live feed medical video consultation. The system includes an imaging booth with a plurality of cameras for capturing body images of a patient, a server for storing and transmitting patient images and patient information, a computer and/or mobile computing device in communication with the server, and a computer processing unit in communication with a program application that includes the ability to conduct or schedule a live feed video consultation between the patient and a medical provider where the live feed video consultation enables both the patient and the medical provider to view the patient's body images. The imaging booth may be a foldable total body imaging apparatus that includes a foldable floor to produce a compact folded apparatus having a small footprint when not in use.

16 Claims, 40 Drawing Sheets

(51) Int. Cl.
*G16H 30/20* (2018.01)
*G16H 80/00* (2018.01)
*H04L 65/403* (2022.01)
*H04L 67/12* (2022.01)

(56) References Cited

U.S. PATENT DOCUMENTS

| | | | |
|---|---|---|---|
| 2016/0069062 A1* | 3/2016 | Dynon | E04B 1/343 |
| | | | 52/79.5 |
| 2016/0247017 A1* | 8/2016 | Sareen | A61B 5/7475 |
| 2017/0335561 A1* | 11/2017 | Wickramasekera | E04H 1/1205 |
| 2020/0165030 A1* | 5/2020 | Song | B65D 25/24 |

* cited by examiner

NOTES:
1. Install electrical components.

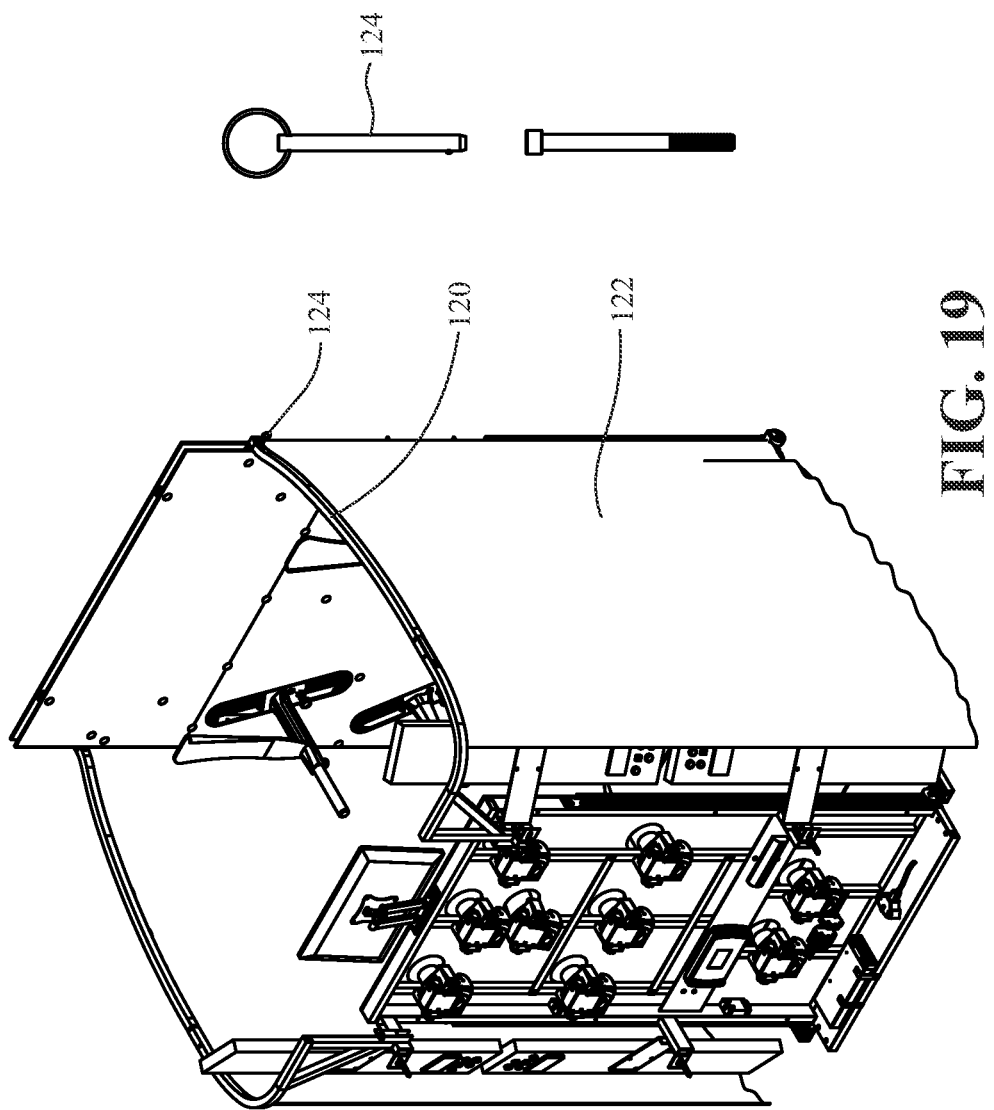

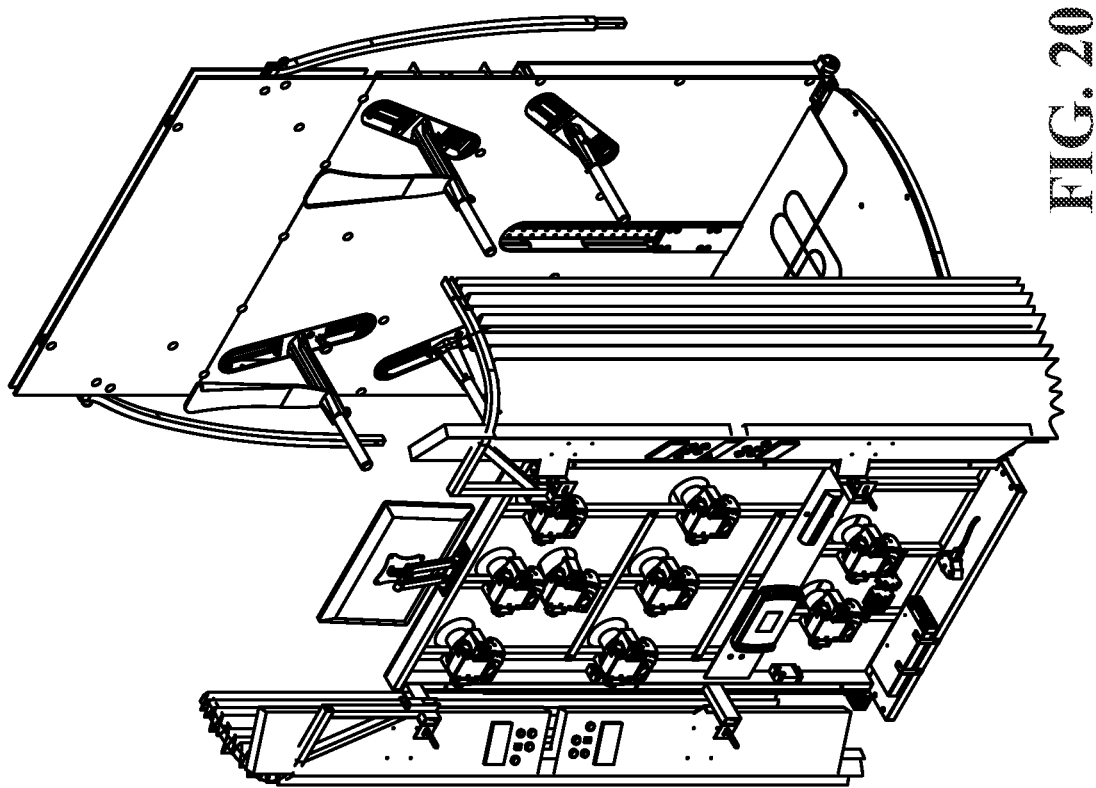

FIG. 26

SYSTEM AND APPARATUS FOR ASYNCHRONOUS TOTAL BODY IMAGING WITH SYNCHRONOUS LIVE FEED VIDEO CONSULTATION

CROSS-REFERENCE TO RELATED APPLICATIONS

This patent application claims priority to provisional patent application having Ser. No. 63/056,223, filed Jul. 24, 2020, which is herein incorporated by reference in its entirety. This patent application also relates to U.S. pending utility patent application having Ser. No. 15/727,487, U.S. issued U.S. Pat. No. 10,238,293, and U.S. issued U.S. Pat. No. 10,702,159, all of which are herein incorporated by reference in their entireties.

FIELD OF INVENTION

The present invention generally relates to system and apparatus for automated total body imaging which includes a compact foldable imaging booth with live feed video consultation capability. More particularly, the present invention relates to a system and apparatus for automated total body imaging which includes a streamlined foldable imaging station/booth having a small footprint for use in medical offices which is capable of quickly, efficiently, effectively and consistently capturing multiple body images of a user or patient with minimal assistance from medical staff. The multiple digital body images of the user/patient are stored and the imaging booth provides a live feed video connection capability so that the user/patient can have a video consultation with the user/patient's physician or dermatologist after capturing and storing of the user/patient's skin images. Alternatively, the user/patient may have a live feed video consult with a pre-designated online medical provider immediately following the capturing and storing of the user/patient's skin images.

BACKGROUND OF THE INVENTION

Skin related conditions and diseases, including skin cancer, must involve monitoring of the skin in order to diagnose and/or monitor the condition or disease as well as evaluate treatment for the condition or disease. In addition, skin must be monitored to identify skin related side effects and events related to evaluating experimental as well as well established treatments for various diseases.

Skin cancer is the most common form of cancer in the United States. Each year there are more new cases of skin cancer than the combined incidences of breast cancer, prostate cancer, lung cancer, and colon cancer and, over the past 31 years, more people have had skin cancer than all other cancers combined. Each year, more than 3.5 million cases of skin cancer are diagnosed in the U.S.

There are three main types of skin cancer—basal cell carcinoma, squamous cell carcinoma, and melanoma. Basal cell carcinoma is the most common form of skin cancer and an estimated 2.8 million people are diagnosed annually with it in the U.S. Basal cell carcinomas are rarely fatal but can be highly disfiguring if allowed to grow. Squamous cell carcinoma is the second most common form of skin cancer. An estimated 700,000 cases are diagnosed each year in the U.S. and result in approximately 2,500 deaths.

Melanoma is a third form of skin cancer and is the most common form of cancer for young adults ages 25 to 29 and the second most common form of cancer for young people aged 15 to 29. Melanoma is the fifth most common cancer for males and the sixth most common cancer for females. The incidence of melanoma continues to rise and one in 55 people will be diagnosed with melanoma in their lifetime. The survival rate for people whose melanoma is detected early, before the tumor has penetrated the skin, is about 99 percent. However, the survival rate falls to 15 percent for those with advanced disease.

The total direct cost associated with the treatment for nonmelanoma skin cancer in 2004 was 1.5 billion dollars. The number of nonmelanoma skin cancers in the Medicare population went up an average of 4.2 percent every year between 1992 and 2006. Melanoma treatment costs total about 249 million dollars annually for adults 65 and older. Although they only account for three percent of melanomas, about 40 percent of the annual cost for melanoma treatment goes to treating stage IV cancers.

Although skin cancer cases are on the rise, early detection of skin cancer can play a significant role in its treatment and the costs associated with treatment. Self-exams coupled with yearly skin exams by physicians are the best way to achieve early detection. Accordingly, there is a need for quick, efficient, effective and consistent body imaging of individuals/patients so that a physician can easily examine the body images of the individual/patient for skin neoplasms and/or skin variations that require further examination. In addition, there is a need for an automated body imaging system to document and monitor the skin for a number of reasons in addition to skin cancer surveillance. These reasons include, but are not limited to, identification of skin related side effects/events in clinical trials, evaluation of clinical response to a variety of experimental and well established treatments for the management of psoriasis, cutaneous lymphoma, hypersensitivity reactions, etc., cosmetic procedures, and any other application where skin imaging may be useful.

Although several methods and apparatus exist in the prior art for imaging and recording a patient's skin, the present invention was created to efficiently, effectively, and easily display skin images and identify and record observations relating to those skin images including skin abnormalities and areas of concern. The present invention was also created to easily make side by side image comparisons of the same areas of the skin taken at different times and to enable sharing of those displayed images, compared images, and recorded observations relating to those images with patients, health care workers, and health care related entities, and to also enable a live feed video consultation between a patient and a healthcare/medical provider at the location of and/or within the imaging booth itself immediately after taking and recording the images to review and discuss the displayed and compared images.

Alternatively, a patient can elect to schedule a synchronous live feed view consultation with a medical provider at a later date and time after the patient has had his or her body images taken using the imaging station/booth. This ability to schedule a later live feed video consultation between patient and medical provider is part of a program application that is included in the present invention.

The present invention was also created to provide a compact foldable imaging booth/station that can be easily incorporated into a small space/area including areas within a medical office that enable automated full body imaging of a user/patient without taking up a lot of floor space.

SUMMARY OF THE INVENTION

The present invention is directed toward a foldable automated system and apparatus for total body imaging which includes a foldable imaging station/booth for automatically capturing body images of a user when the user is positioned in predetermined poses and then saving and sending the user's total body images to enable the user to conduct a live feed video consultation with the user's medical provider or a pre-designated online medical provider. The live feed video consultation between the user and the medical provider may occur immediately after obtaining and sending the user's total body images to the medical provider or at a later scheduled time between the user and medical provider. The live feed video consultation between the user and the medical provider may occur within the foldable imaging station/booth via the user/patient monitor or using the user/patient's own computer, tablet or mobile device in the comfort of the user/patient's own surroundings. The predetermined poses enable thorough and accurate viewing for detecting skin abnormalities on the user and the user is given an audio and/or visual step by step guide through the poses. The system determines if the user is correctly positioned for a predetermined pose and communicates successful positioning to the user before automatically capturing the body image of the user with one or more cameras.

Key features of the foldable imaging station/booth of the present invention include, but are not limited to, a compact and small footprint for the station/booth itself due to a foldable booth floor that enables the station/booth to be retained in a folded position while not in use, patient privacy during imaging, display screen(s) in the station/booth which guide users through the poses for total body imaging, sensors in communication with positioning indicia and/or positioning members (such as handles, footprints, and/or handprints) to determine correct positioning for a pose and communicating successful positioning to the user, and saving the user's total body images followed by sending the user's total body images to a medical provider for a live feed video consultation between the user and the medical provider.

Key features of the automated system for full body imaging of the present invention include, but are not limited to, rapid/quick collection of precise total body imaging, automated imaging acquisition by guiding users through positions and determining and communicating correct positioning via sensors, patient privacy during imaging, and wireless access to images so that medical professionals can determine skin abnormalities and/or make diagnoses without the need to be present during imaging or at the site of imaging. Another key feature of the automated total body imaging system of the present invention is its ability to interface with electronic medical records (EMRs). An electronic medical record (EMR) is a computerized medical record created in an organization that delivers care such as a hospital or physician's office. Still another key feature is the ability to conduct and/or schedule a live feed video consultation between a patient/user and a medical provider immediately after, or sometime after, the taking and storing of the total body images of the patient/user.

In one exemplary embodiment, the system for total body imaging of the present invention includes i) a foldable imaging station/booth having one or more body positioning indicia or body positioning members (such as a handle, footprint, and/or handprint), a sensor in communication with the body positioning indicia and/or body positioning members, one or more cameras, one or more lighting elements, a foldable floor or bottom, and one or more display screens, ii) a program application in communication with the imaging station/booth for guiding a user through one or more predetermined poses via the display screen in the imaging station/booth, capturing the user's images in each predetermined pose via the one or more cameras, and documenting notes relating to the images, and iii) a computing device in communication with the program application for storing the images, accessing and viewing the images, and inputting information relating to the images. The computing device may be connected (i.e. wired) to another computing device to enable a medical professional/medical provider to access user images and data. In addition, the computing device may be connected (e.g. wired) to a visual display and/or computing device that enables a technician/medical assistant to control capture of the user images by use of a graphic user interface specifically designed for the technician/medical assistant.

The system may also include a server in communication with a network so that user images can be wirelessly accessed by medical professionals through the wireless network and the medical professional can document notes and/or comments relating to the images and also conduct live feed video consultations with the patient/user whose total body images have been obtained and stored. In addition, the server may access external databases to aid the medical professional in analyzing the user images. In particular, the system for total body imaging of the present invention may interface with electronic medical records (EMRs). The total body imaging system of the present invention may deliver imaging results in the form of EMRs to a physician, medical professional, and/or medical facility such as a hospital or clinic and/or the total body imaging system of the present invention may interface with existing EMR databases from other medical providers and/or facilities for individuals/patients that undergo the total body imaging of the present invention so that the total body imaging of the present invention can also be compared to the EMRs in those other databases.

The one or more body positioning members may include one or more handles for the user's hands and a footplate for the user's foot or feet and the handles and/or foot plate may each include a light emitting component with capacitive touch sensor to enable the handles and/or footplate to light up when properly engaged by the user when performing the predetermined body pose(s). In addition, the footplate may be vertically moveable and retractable within the floor of the foldable total body imaging station/booth. As seen in one exemplary embodiment, the plurality of cameras may include a camera with a wide angle lens positioned to capture the total body image of a user and a plurality of high resolution cameras positioned to capture different body portions or body parts of the user. The foldable total body imaging station/booth may also include a panel positioned in front of the cameras having a plurality of circular openings so that a lens from each of the cameras can be seen through each of the circular openings, respectively. Further, the light panel in the foldable total body imaging station/booth may include two light panels positioned on opposite sides of the cameras and the panel positioned in front of the cameras may also include at least two vertically oriented openings so that a front of each of the light panels can be inserted into each of the two vertically oriented openings, respectively.

The foldable total body imaging system of the present invention includes a wide angle lens camera positioned to capture a total body image of a user, a plurality of high resolution cameras positioned to capture different body portions of the user's total body where the wide angle lens camera and the plurality of high resolution cameras capture images simultaneously, and a computer processing unit in communication with at least one program application that arranges high resolution body part images taken with the plurality of high resolution cameras for a particular pose and associates them with the total body image of the user captured with the wide angle lens camera. The program application may use the total body image taken with the wide angle lens camera as a navigational grid by sectioning the total body image into sections that correspond to the location of the plurality of high resolution cameras and their related high resolution body part images where any of the sections can be selected and magnified to further view in more detail an area of skin contained within the selected section.

The program application may further include a reduced size image of the sectioned navigational grid displayed on a magnified image of a selected section of the navigational grid that has been selected for viewing in more detail. The program application may also include the ability to further magnify and also annotate the high resolution body part image that is associated with the selected section of the total body image navigational grid.

In addition, the program application of the present invention may also include additional abilities and features including the ability to draw one or more different boundary configurations around areas of concern identified in the images, the ability to descriptively identify the location on the body of the areas of concern as well as the ability to notate comments and observations about the areas of concern, the ability to record a diagnosis and/or medical code relating to the areas of concern, the ability to compare the area or areas of concern with previous recorded images of the same area or areas of concern to enable a side by side comparison of the area or areas of concern taken at different times, and the ability to share images of concern with the user/patient, other healthcare professionals, and/or health care related entities via a wired and/or wireless connection. The program application also includes the ability to conduct or schedule a live feed video consultation between a user/patient and healthcare professional/medical provider.

The foldable total body imaging station/booth may also include a computer processing unit in communication with one or more program applications related to the use of the foldable total body imaging station/booth. The program application(s) may include a program application for guiding a user through a series of one or more predetermined body poses by utilizing the imaging display device and/or the speaker component(s). The program application(s) may also include a program application for taking, capturing, and storing the images obtained from the plurality of cameras. The program application(s) can also include an automatic focusing algorithm to automate the focusing of the plurality of cameras by determining an area of interest for each camera in each of the predetermined body poses that are undertaken by a user. The program application(s) may also include a program application that enables a medical professional and/or medical facility (such as hospitals, medical clinics, etc.) to obtain wireless access to the images in order to view the images, compare a plurality of the images of a same user taken at different times, document notes relating to the images, create electronic medical records that include the images, and/or send the images and related notes to another medical professional and/or medical facility. Further, the program application(s) can include a program application that enables a medical professional and/or medical facility having access to the images of a user to interface with other existing electronic medical record databases from other medical professionals and/or medical facilities utilized by the user so that the images of the user can be compared to other existing electronic record databases. The total body imaging station/booth may also include a technician computer device located outside the enclosed interior area that enables a technician to control one or more of the program applications.

The present invention is also specifically directed to a system that combines asynchronous high resolution full body imaging of a patient/user utilizing an imaging booth with a synchronous live feed video consultation between the patient/user and the patient's/user's medical provider (or a pre-designated medical provider). The synchronous live feed video consultation between patient/user and medical provider that occurs after total body imaging of the patient/user can include viewing of the full body images that were obtained utilizing the imaging booth and a review/discussion of the same to determine treatment, further tests, further follow up, etc. The combined asynchronous high resolution full body imaging of a patient/user utilizing an imaging booth with a synchronous live feed video consultation between the patient/user and the patient's/user's medical provider enables medical providers to provide a majority of dermatological care remotely and enables medical providers to view and determine/diagnose almost any skin conditions without having to see the patient in person.

The system's synchronous live feed video consult between patient/user and medical provider can occur before, during, and/or after full body imaging of the patient/user using the imaging booth. In the case of a synchronous live feed video consult before imaging with the imaging booth, the medical provider may discuss any skin issues/concerns with the patient/user and then order full body images of the patient/user using the imaging booth. In the case of a synchronous live feed video consult during imaging with the imaging booth, the medical provider may order and schedule full body imaging of the patient/user utilizing a specific imaging booth and then observe via live feed video the taking of the full body images of patient/user and then review and discuss the full body images with the patient/user either at the imaging booth using a display screen(s) in the imaging booth or during a later scheduled time with the patient/user. With synchronous live feed video consultation occurring during the taking of the full body images of the patient/user, the medical provider can decide if certain images showing certain areas of the patient's body are adequate or need to be retaken to enable the medical provider to conduct an accurate virtual total body screening of the patient/user's skin.

In the case of a synchronous live feed video consult after imaging with the imaging booth, the medical provider can provide the patient/user with information and instructions on where to obtain full body imaging utilizing an imaging station and then the synchronous live feed video consult between patient/user and medical provider can occur in the imaging booth via the display screen(s) in the imaging booth immediately following the patient/user imaging or, alternatively, the synchronous live feed video consult between patient/user and medical provider can occur later at any time and place scheduled by the medical provider. For example, the synchronous live feed video consult between the patient/user and medical provider could occur at any later scheduled time using a program application that enables the medical provider and patient/user to connect via live feed video on their respective computers, tablets, cell phones, etc. to view and review/discuss the patient/user's total body images utilizing image viewing software. Depending on a medical provider's preference and availability to review the patient/user's total body images taken using the imaging booth, the synchronous live feed video consult between patient/user and medical provider could occur minutes, hours, days or weeks after the taking and collecting the images. Moreover, the imaging booths used to obtain the patient/user full body images may be located at any number of places other than a private doctor's office including, but not limited to, community health centers, Telehealth centers, outpatient centers, etc. This enables the patient/user's medical provider or any pre-designated medical provider to schedule and conduct full body screening of a patient's skin and consultation with the patient/user directed to the full body screening without an "in person" medical office visit.

The system's asynchronous high resolution full body images of a patient/user that are obtained using an imaging booth are saved and sent to the patient/user's medical provider or a pre-designated medical provider. The full body images of the patient/user may also be saved to a cloud system that can be accessed by the patient/user's medical provider or a pre-designated medical provider. After the system's synchronous live feed video consult between the patient/user and medical provider, the medical provider may discard and delete the patient/user images or may save the images for comparison to later full body images taken of the same patient/user. The total body images of patients/users taken with the imaging booths may be saved to perform further analytics and medical providers may even subscribe to a separate entity that provides analytics on the images.

The system of the present invention enables medical providers, and particularly all dermatologists, to schedule and conduct virtual skin exams of a patient/user's full body without "in person" patient contact and visits. In addition, the system of the present invention may be used in situations where a patient/user has specific concerns about a skin issue/abnormality or wants full body imaging as a preventative measure and as baseline images for the future. In this instance, if the patient/user does not already have a designated medical provider, they can go to an imaging booth, obtain full body images and then connect an available and/or pre-designated online derm/medical professional to see if further consult is needed—i.e., a preventative telemed visit that may eventually be pre-approved for insurance without the need for a medical provider's referral/scrip.

Teledermatology allows these types of assessments to be made from geographically remote locations or rural areas. Currently, however, teledermatology is limited to photographs of individual lesions which are difficult to compare with photographs taken at other points in time. High resolution standardized image collection, storage, and analytics, which are specialized for obtaining serial full-body skin images combined with the capability of a live feed dermatological consultation simulates an "in office" skin exam.

This system offers standardized imaging, given its enclosed booth with patient-customized handlebars and footrest to allow for consistent body positioning in the most efficient space. It maximizes patient privacy and requires much less set-up and training than the other platforms, also attributable to its booth design and highly automated imaging process. Patients are guided through each of the poses by an instructional video that plays inside the booth, and operators outside the booth need only minimal training in order to operate the system. Images are uploaded and stored securely in an onsite server and back up cloud server. The Physician Viewer software allows the medical provider to efficiently review total body images, make written comments about lesions or conditions which are tagged to the images, and print a report which includes those images and their corresponding comments. This software can be shared virtually through a live consultation with the patient to communicate the skin evaluation. The report can be scanned into the electronic medical record, thus enhancing the medical record without incorporating the very large original image files.

BRIEF DESCRIPTION OF THE DRAWINGS

The subject invention will hereinafter be described in conjunction with the appended drawing figures which depict portions of the total body imaging apparatus (both Applicant's prior imaging booth design and current foldable design) as well as exemplary screen shots of a graphical user interface (GUI) seen by a physician/healthcare worker and/or a user/patient while obtaining skin care images of the user/patient and viewing skin care images of the user/patient in accordance with the total body imaging system of the present invention and flow charts showing live feed video consultation capability between users/patients and medical providers, and where

FIG. 19 is the same view as shown in FIG. 18 with the addition of side curtain rails attached to the front and rear curtain bracket assemblies and curtains attached to the side curtain rails of the foldable total body imaging apparatus;

FIG. 20 is a perspective view of the foldable total body imaging assembly shown in FIG. 19 with the side curtains shown pushed to the front of the imaging assembly and locked in place and the side curtain rails shown lowered at the point of the upper back wall mountable frame portion and locked in place;

Figure 26:
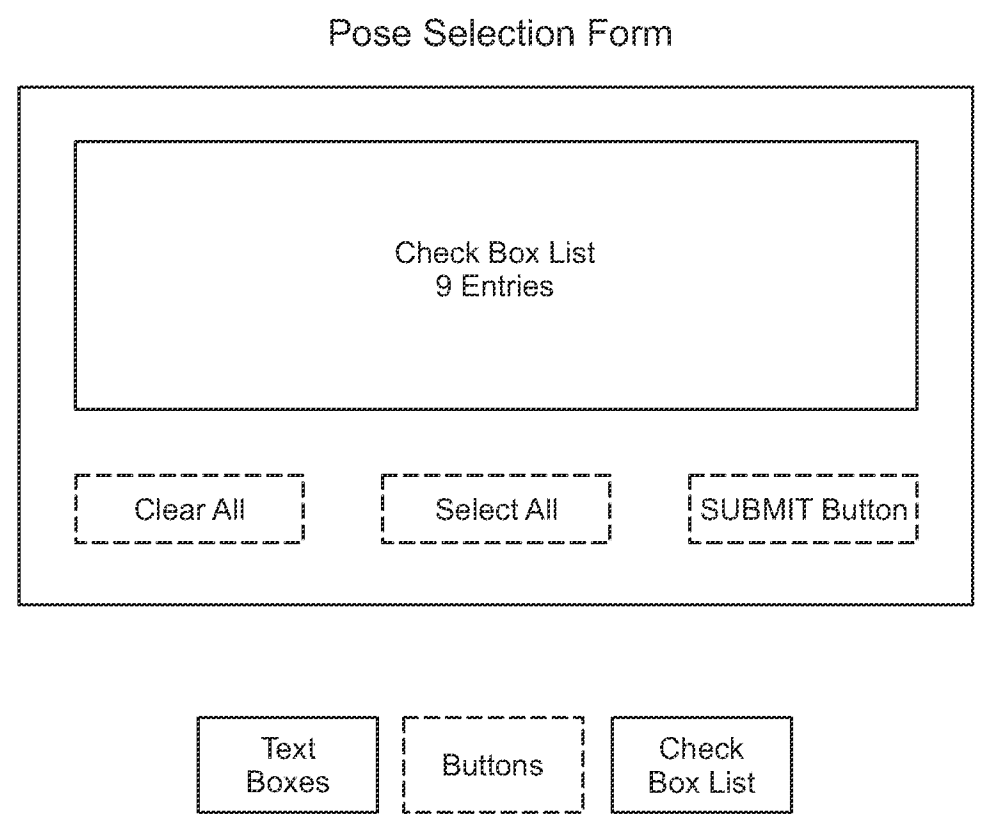

FIGS. 24 through 33 show exemplary frames/screen shots of the graphic user interface for technicians/medical assistants and/or users/patients used with the foldable imaging station/booth to ensure that the automated imaging is correctly carried out and completed wherein each frame/screen shot corresponds to main windows and subsequent pop up windows in the graphical user interface.

DETAILED DESCRIPTION OF EXEMPLARY EMBODIMENTS

Figure 1:
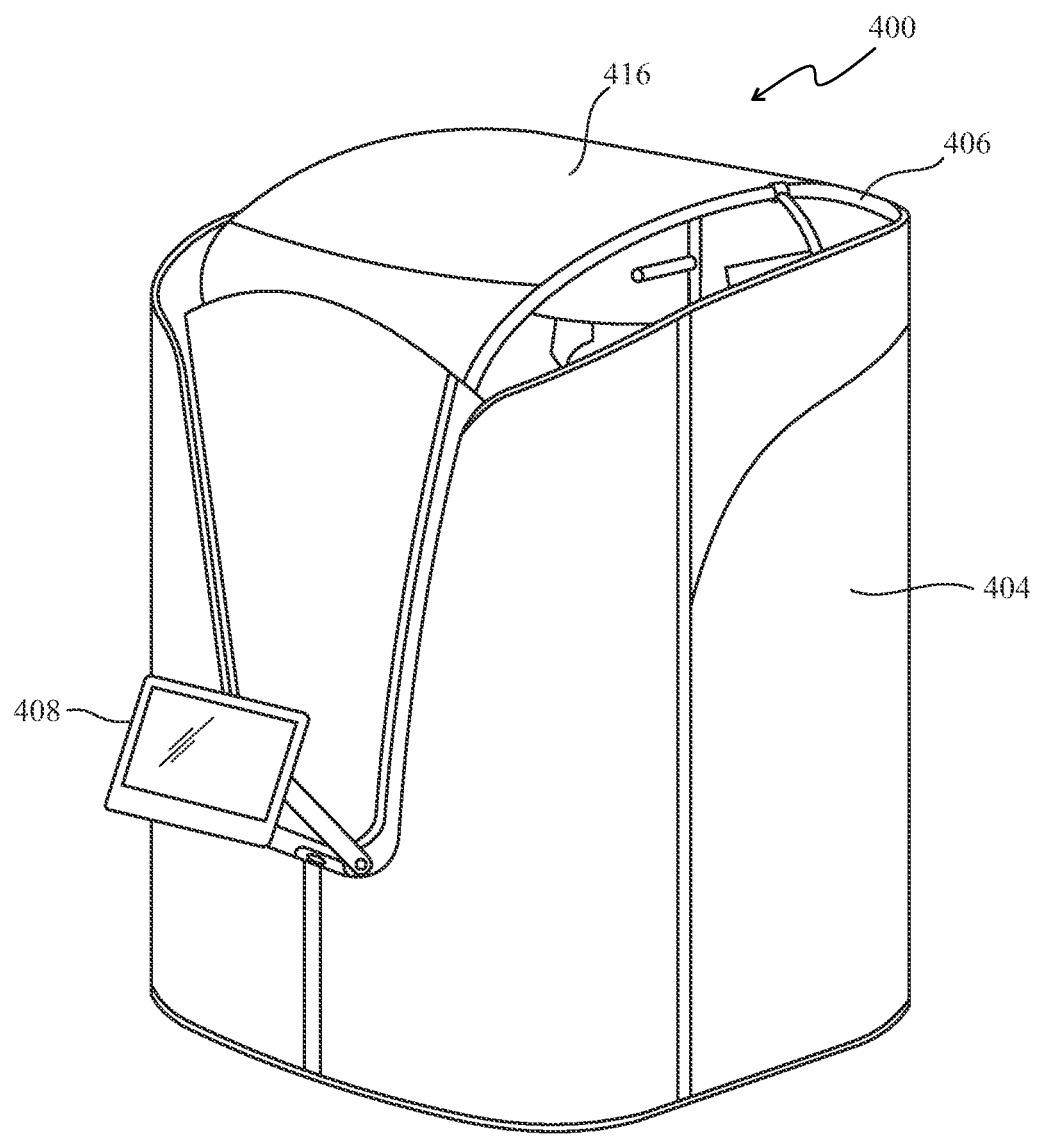
FIG. 1 is an outer perspective view of a prior exemplary embodiment of a total body imaging apparatus/imaging booth that can be used in accordance with the system of the present invention.
Figure 2:
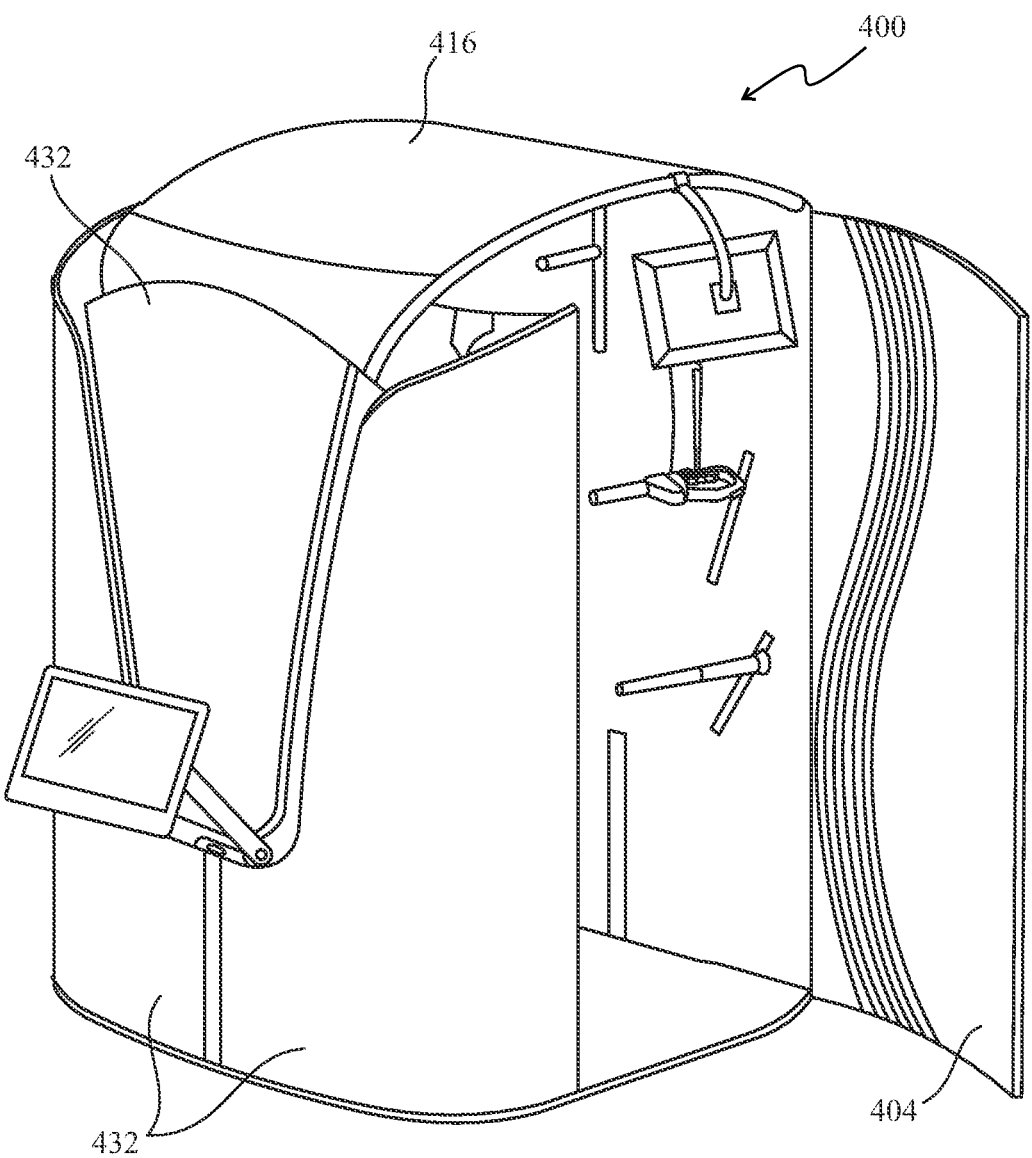
FIG. 2 is an outer perspective view of the prior exemplary embodiment of the total body imaging apparatus/imaging booth depicted in FIG. 1 with a door of the total body imaging apparatus/imaging booth shown open.
Figure 3:
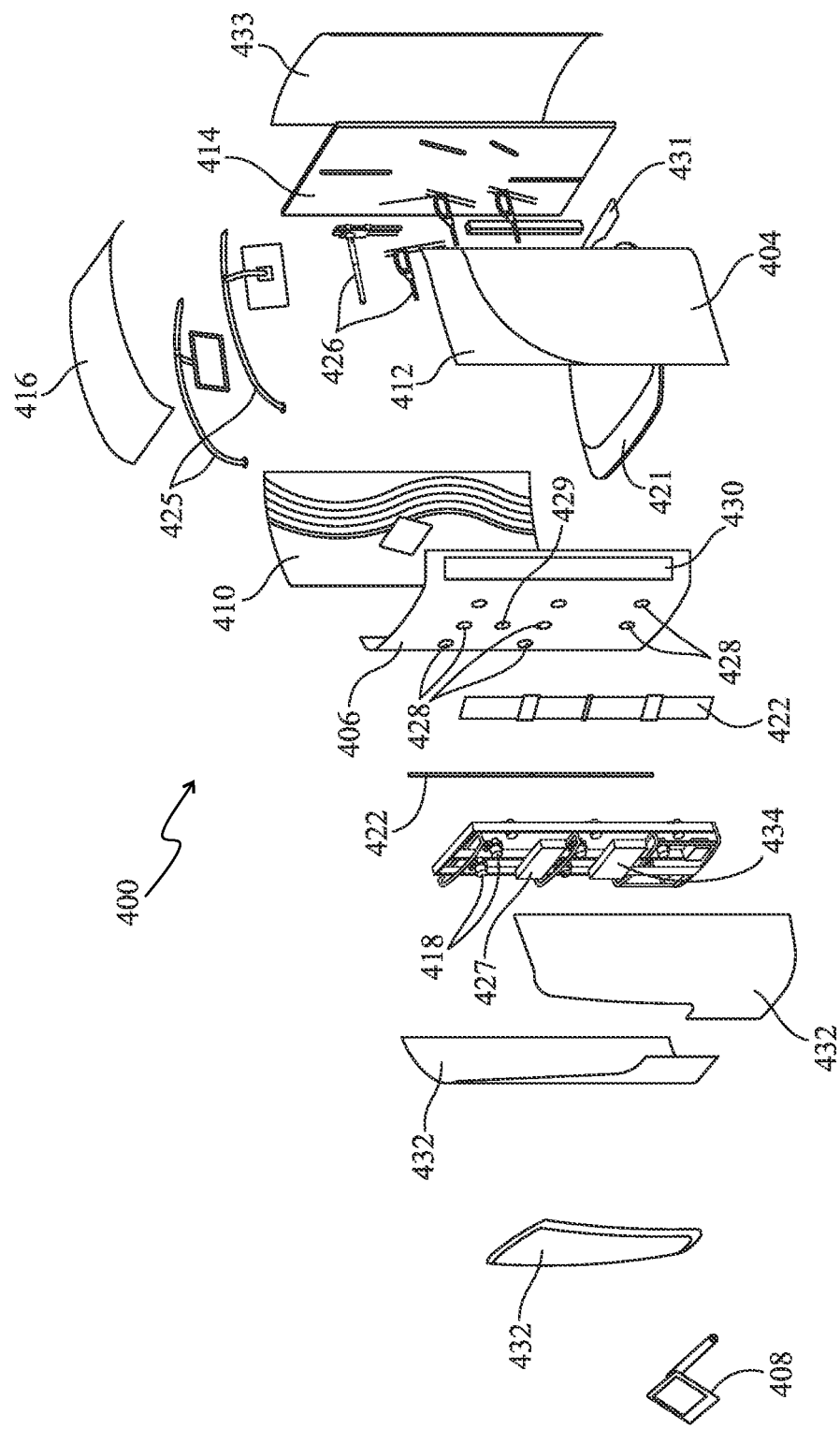
FIG. 3 is an exploded view of the prior exemplary embodiment of the total body imaging apparatus/imaging booth shown in FIG. 1 which also shows several same components contained in the current exemplary embodiment of the foldable total body imaging apparatus of the present invention shown in FIGS. 7-22.
Figure 5:
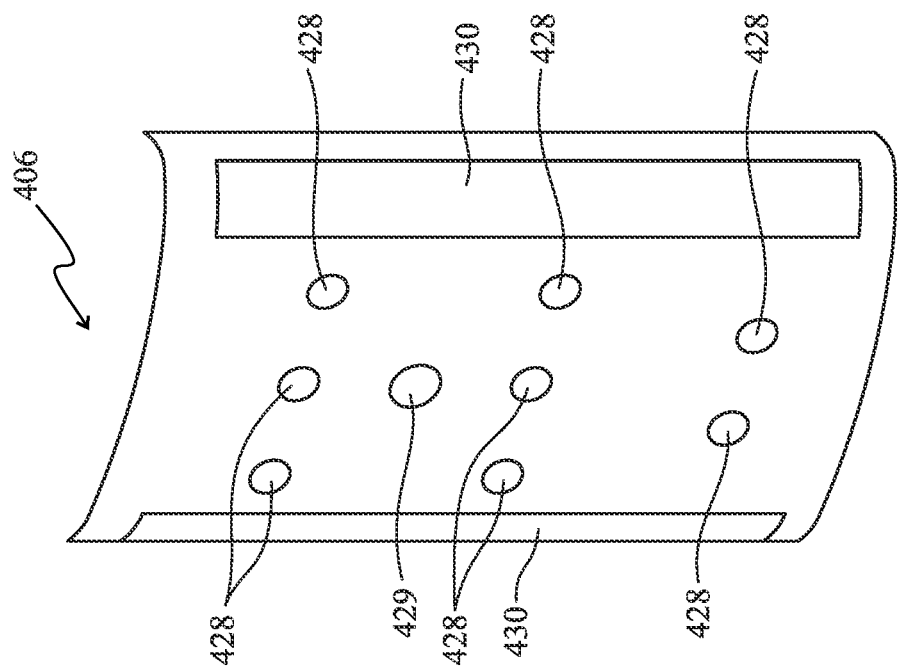
FIG. 5 is a front perspective view of the front panel of the prior exemplary embodiment of the total body imaging apparatus/imaging booth shown in FIGS. 7-22 having openings contained therein for the camera lenses which is also contained in the current exemplary embodiment of the foldable total body imaging apparatus shown in FIGS. 7-22.
Figure 4:
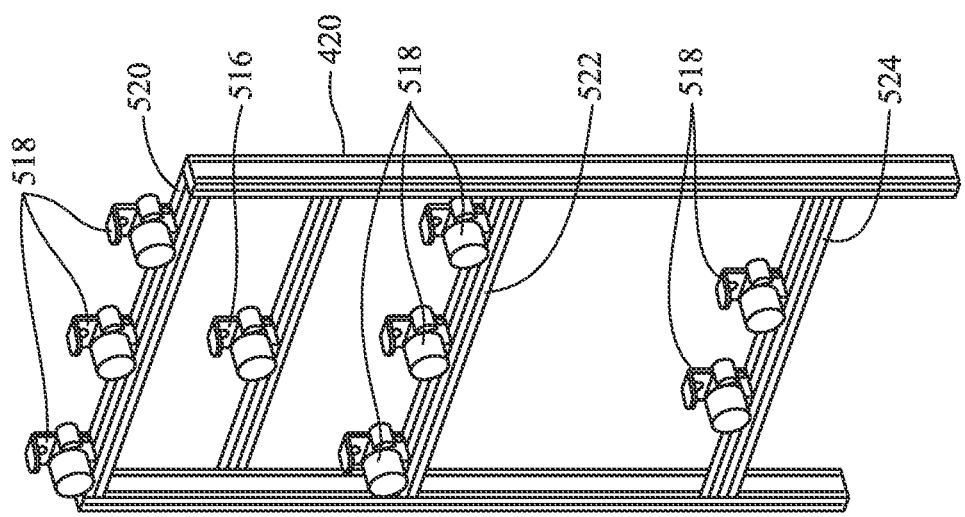
FIG. 4 is a perspective view of the plurality of cameras and the frame which supports the plurality of cameras contained in the prior exemplary embodiment of the total body imaging apparatus/imaging booth shown in FIGS. 1-3 which are also contained in the current exemplary embodiment of the foldable total body imaging apparatus shown in FIGS. 7-22.
Figure 6:
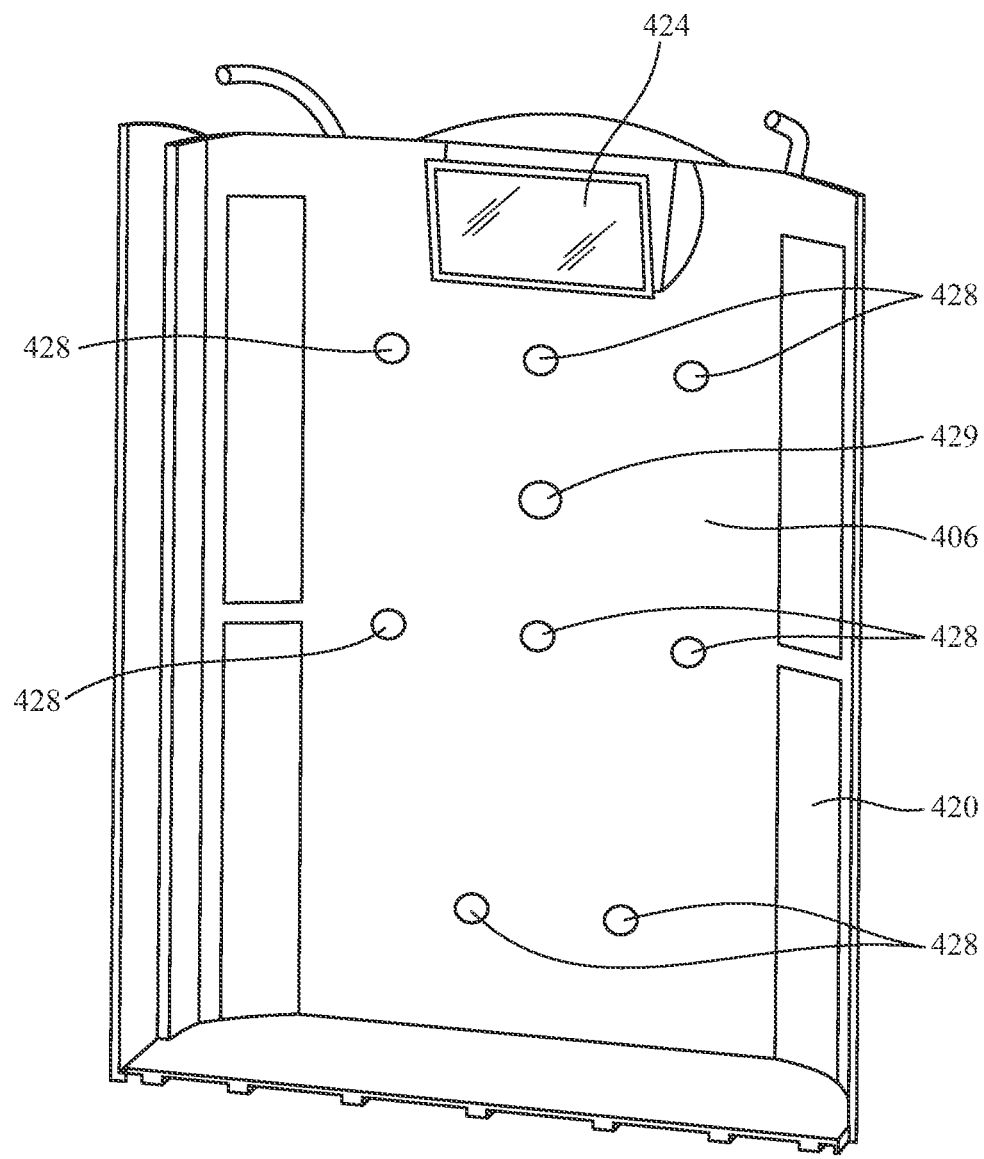
FIG. 6 is a rear perspective view of the front panel of the prior exemplary embodiment of the total body imaging apparatus/imaging booth shown in FIGS. 1-3 and 5 showing the front panel as it looks from standing inside the prior exemplary embodiment of the total body imaging apparatus/imaging booth, a version of which is also contained in the current exemplary embodiment of the foldable total body imaging apparatus shown in FIGS. 7-22.
Figure 7:
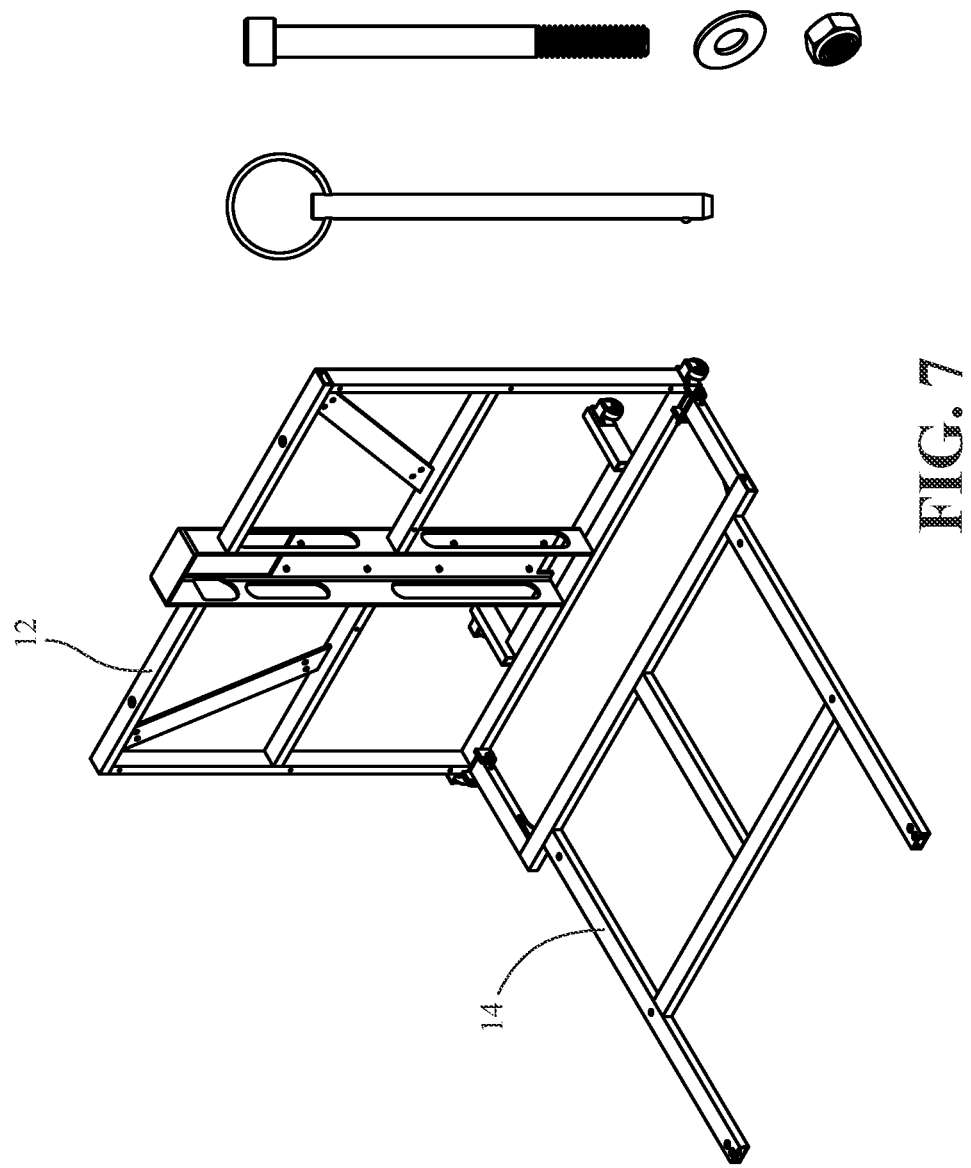
FIG. 7 is a perspective view of the lower bottom frame and the back wall mountable frame portions of an exemplary embodiment of the foldable total body imaging apparatus of the present invention.
Figure 8:
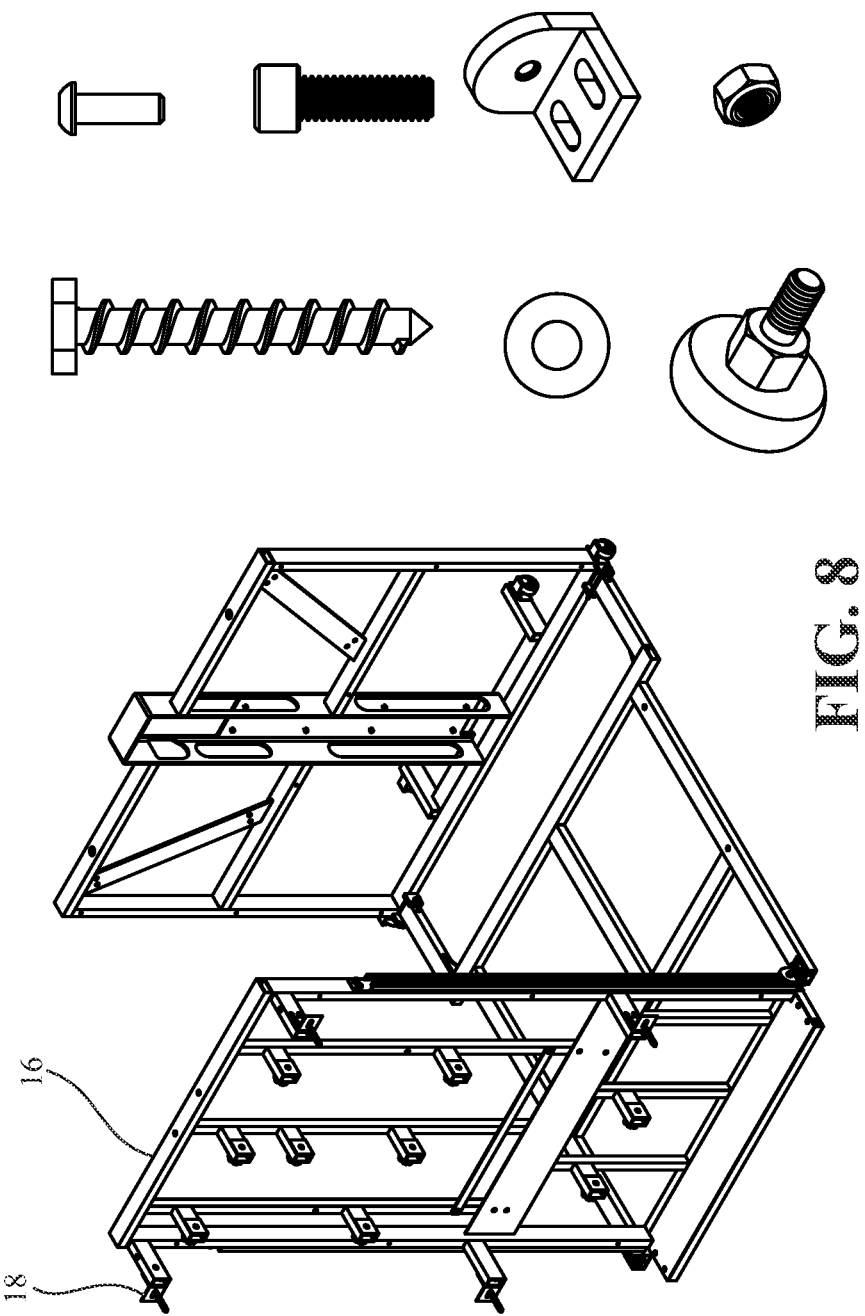
FIG. 8 is a perspective view of the front frame, the lower bottom frame, and the back wall mountable frame portions of the foldable total body imaging apparatus shown connected to one another by a floor frame.
Figure 9:
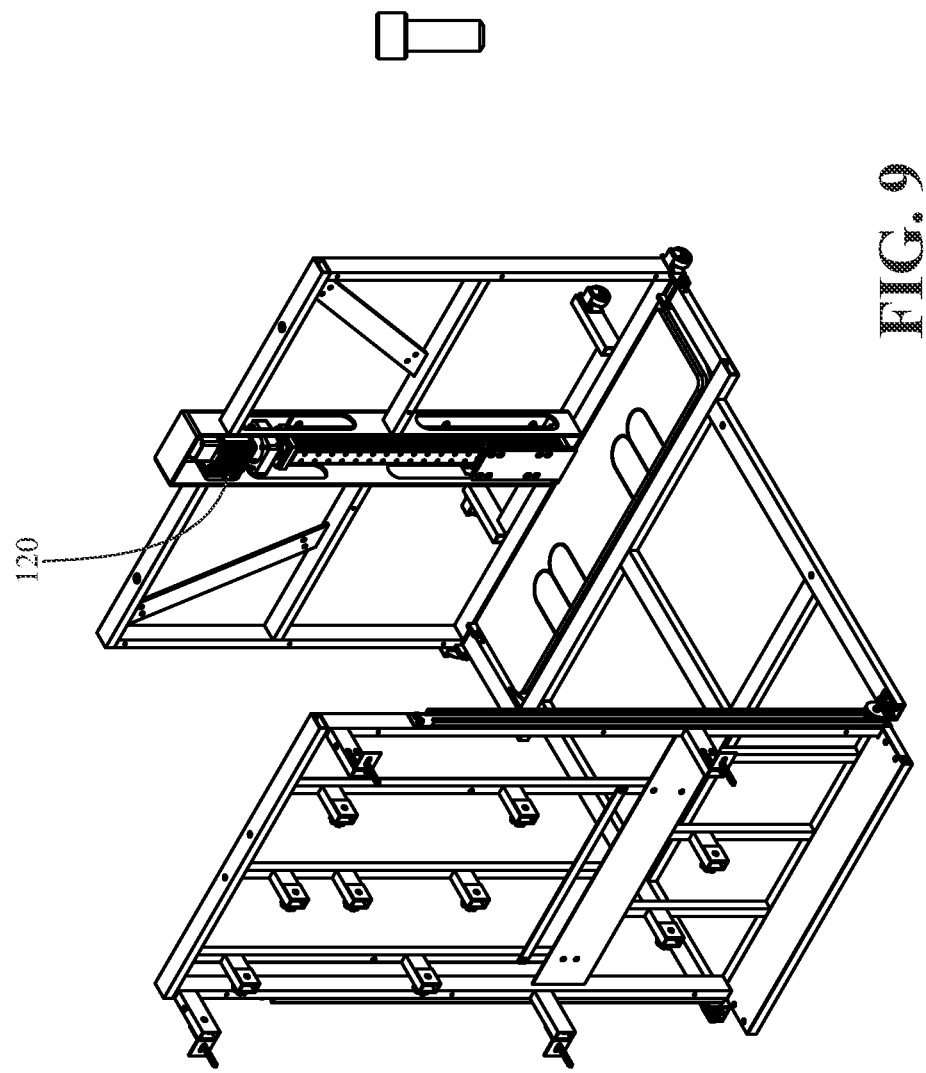
FIG. 9 is the same view as shown in FIG. 8 with the addition of the step actuator shown attached to the back wall mountable frame portion of the foldable total body imaging apparatus of the present invention.
Figure 10:
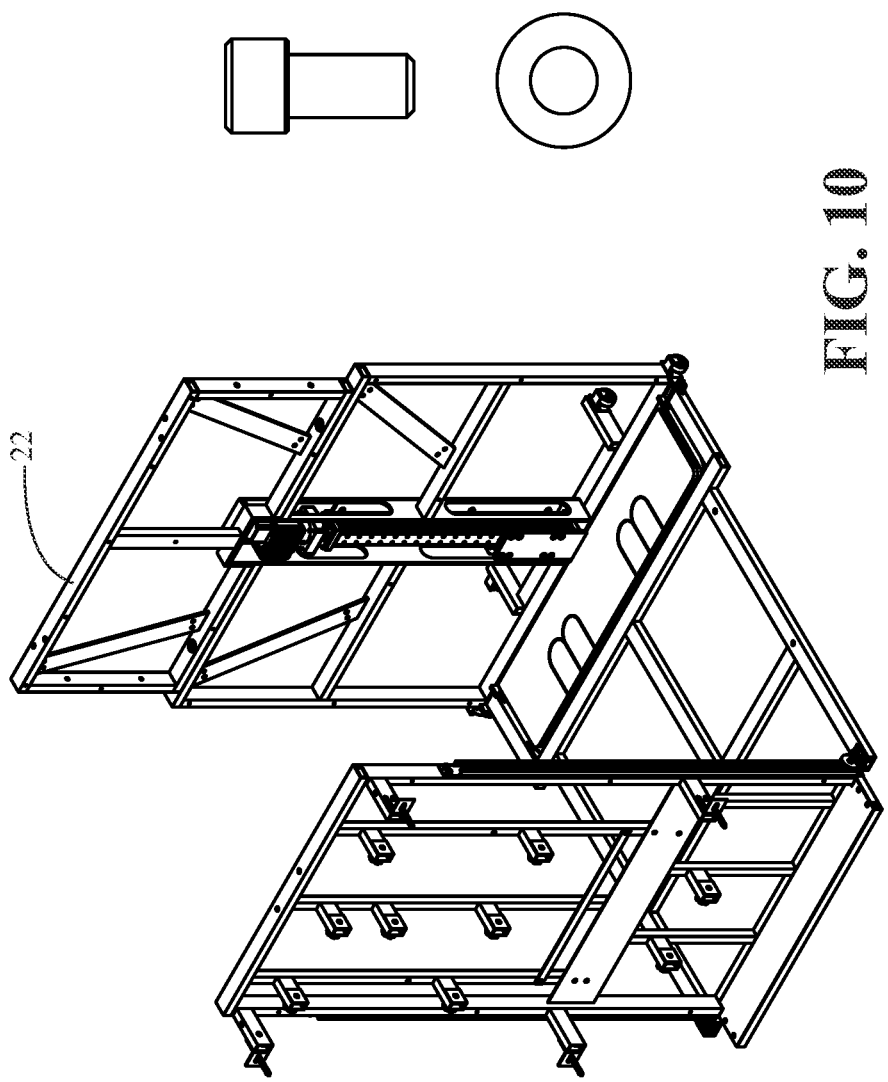
FIG. 10 is the same view as shown in FIG. 9 with the addition of an upper back wall mountable frame portion shown attached to the back wall mountable frame portion of the foldable total body imaging apparatus of the present invention.
Figure 11:
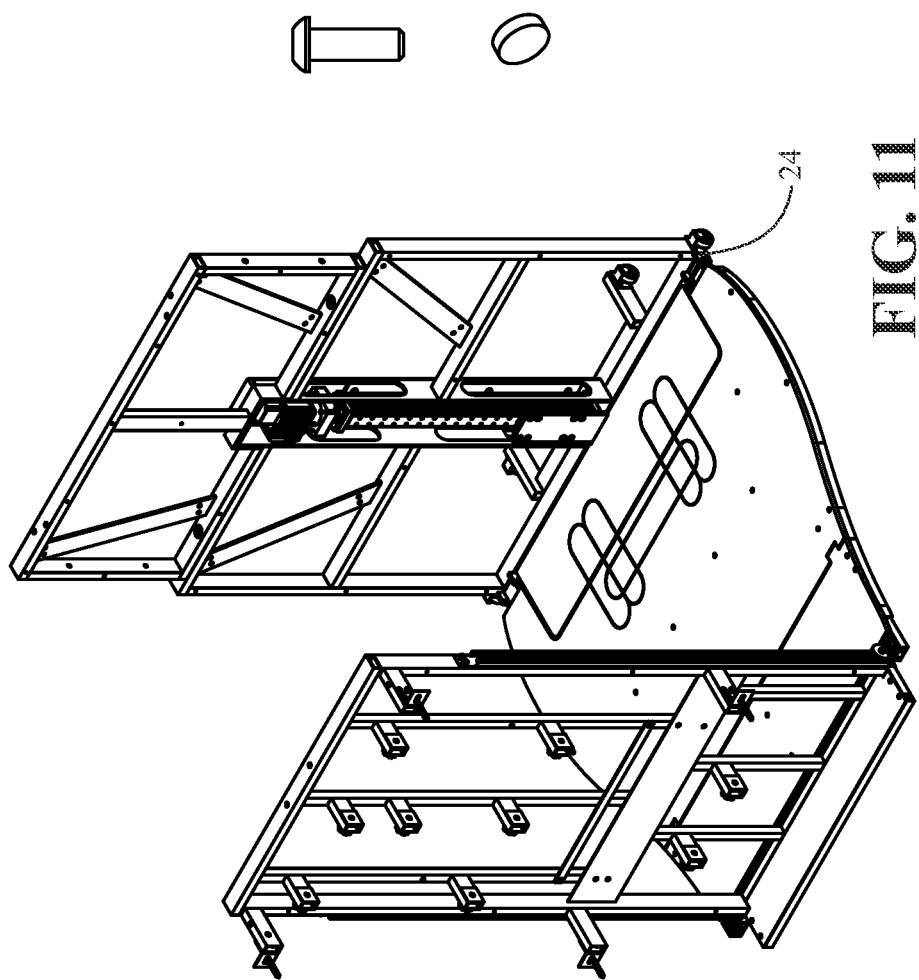
FIG. 11 is the same view as shown in FIG. 10 with the addition of the foldable floor plates shown attached to the lower bottom frame of the foldable total body imaging apparatus of the present invention (note lower bottom frame is also moveable/foldable at same point where foldable floor plates lie adjacent to one another)
Figure 12:
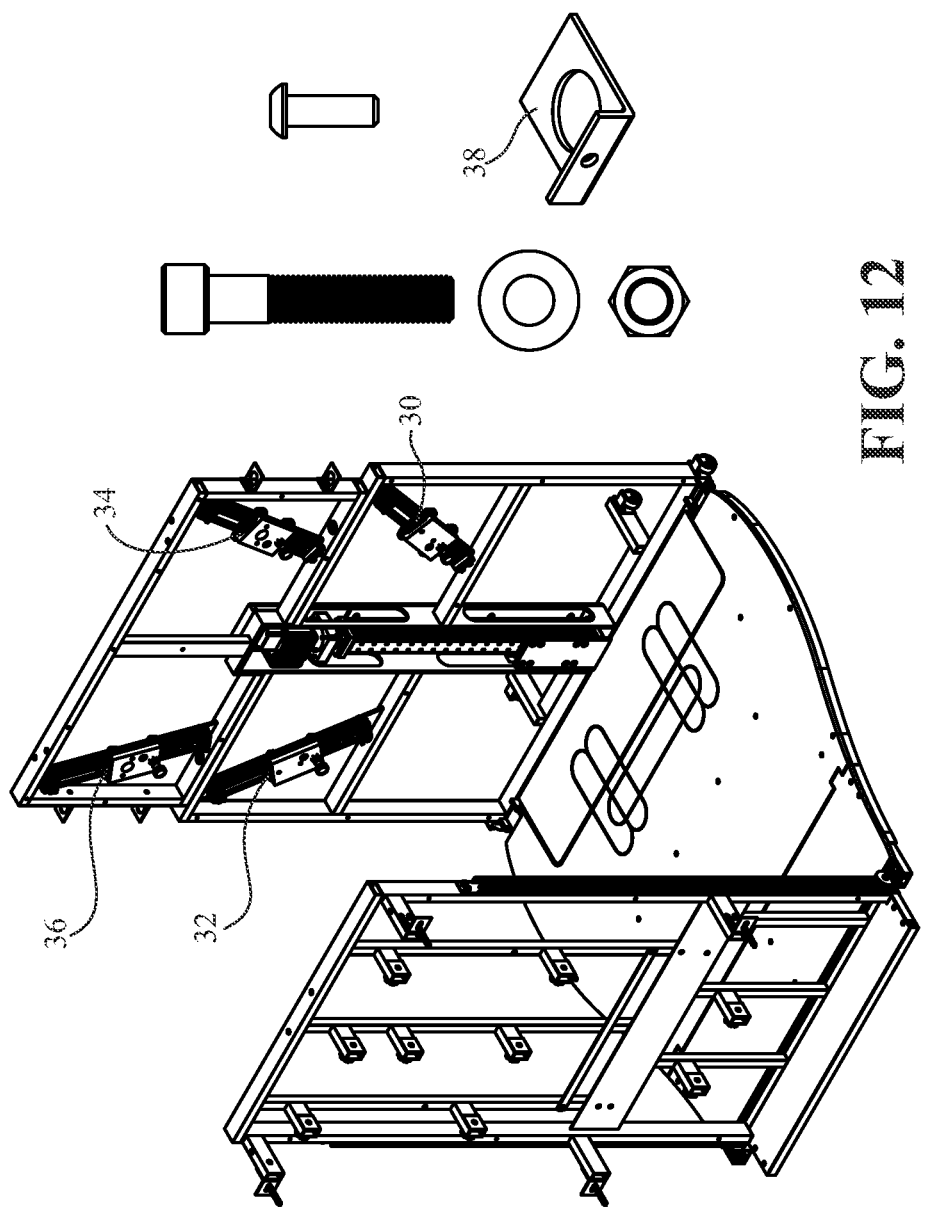
FIG. 12 is the same view as shown in FIG. 11 with the addition of handle sliders and handle brackets shown attached to the back wall mountable frame portion of the foldable total body imaging apparatus of the present invention.
Figure 13:
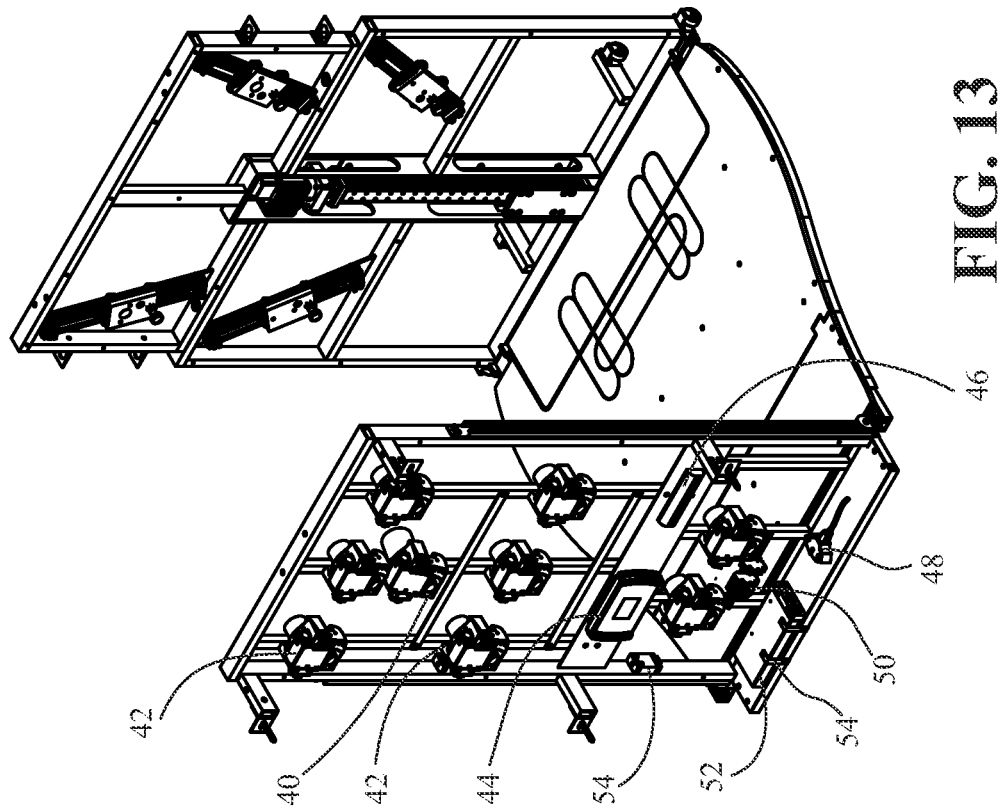
FIG. 13 is the same view as shown in FIG. 12 with the addition of cameras and electrical components for controlling the moveable and functional components of the foldable total body imaging apparatus shown attached to the front frame of the foldable total body imaging apparatus of the present invention.
Figure 14:
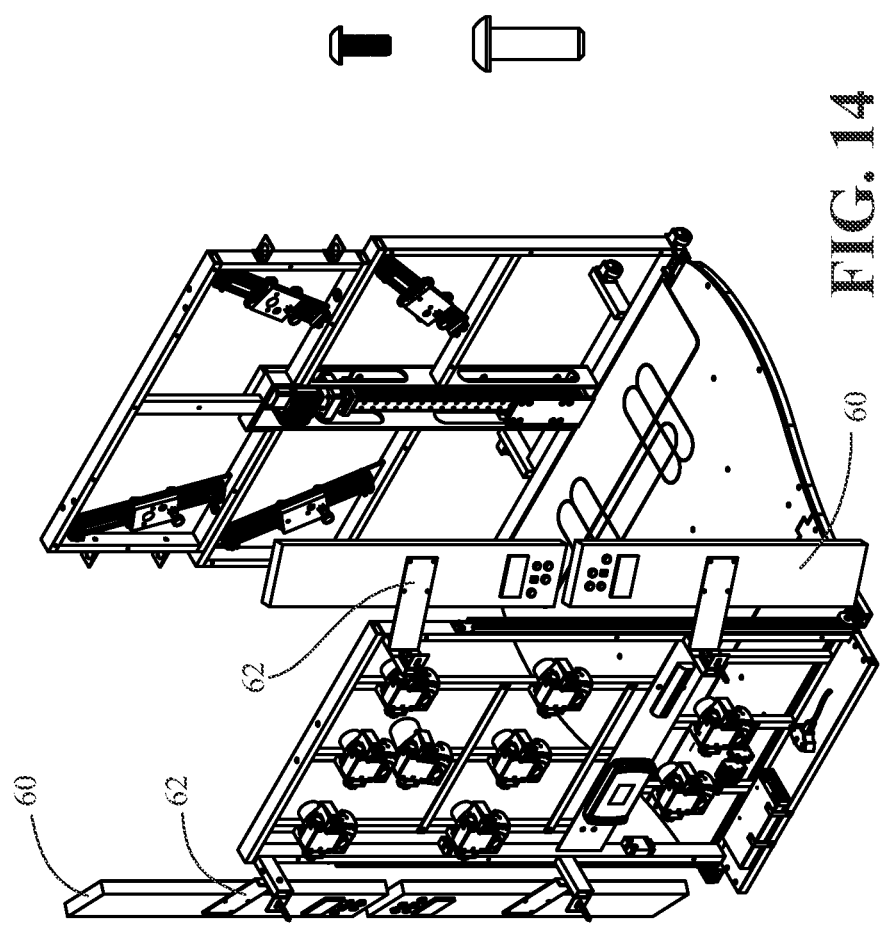
FIG. 14 is the same view as shown in FIG. 13 with the addition of light panels shown attached to the sides of the front frame of the foldable total body imaging apparatus of the present invention.
Figure 15:
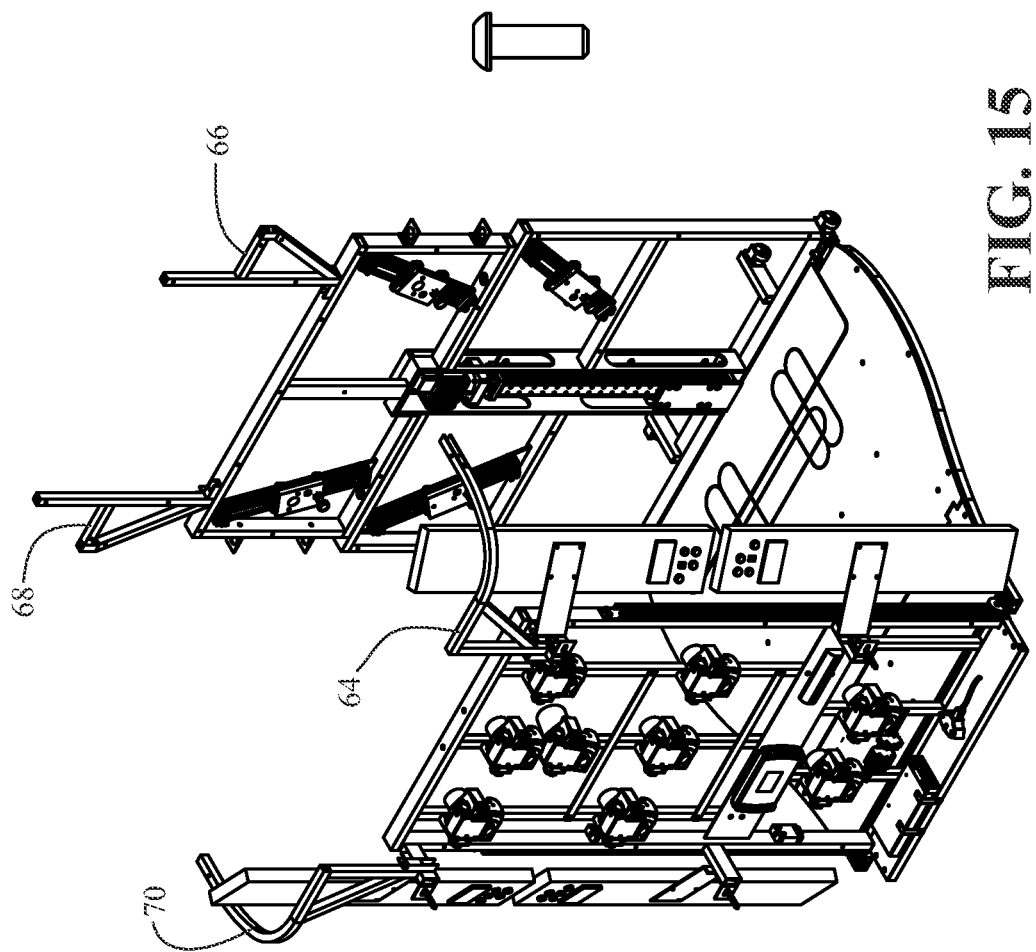
FIG. 15 is the same view as shown in FIG. 14 with the addition of front curtain bracket assemblies shown attached to the front frame of the foldable total body imaging apparatus of the present invention and back curtain bracket assemblies shown attached to the upper back wall mountable frame portion of the foldable total body imaging apparatus.
Figure 16:
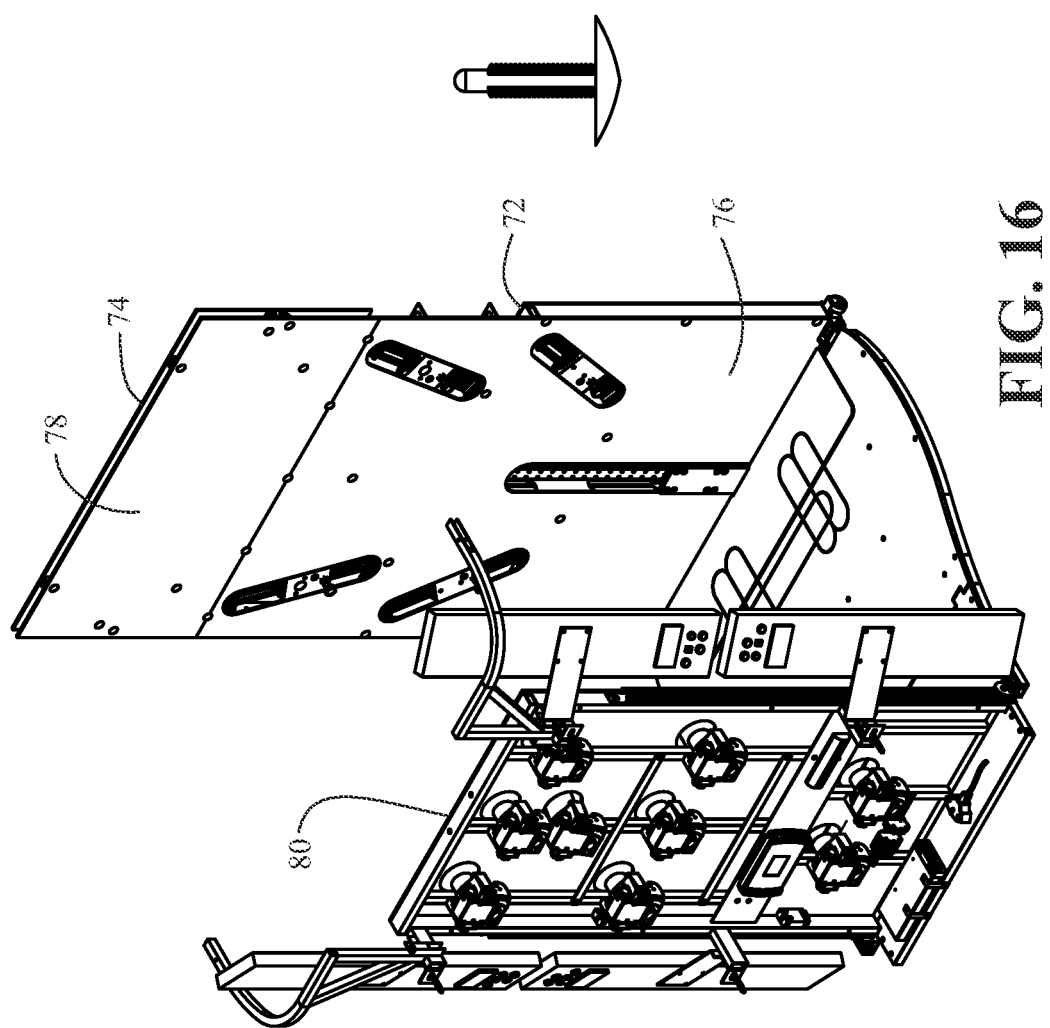
FIG. 16 is the same view as shown in FIG. 15 with the addition of front wall panels shown attached to the front frame facing the interior of the foldable total body imaging apparatus of the present invention and back wall panels shown attached to the upper back wall mountable frame and back wall mountable frame portions facing the interior of the foldable total body imaging apparatus.
Figure 17:
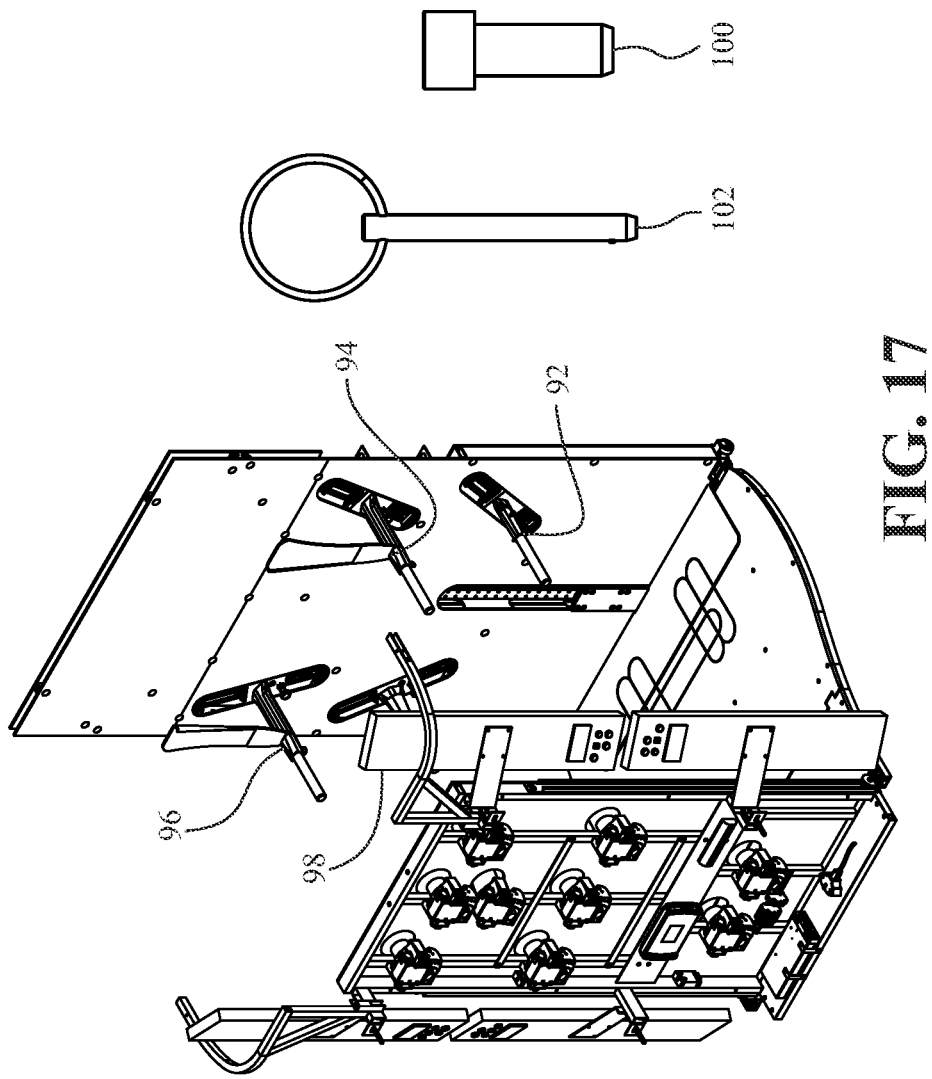
FIG. 17 is the same view as shown in FIG. 16 with the addition of lower and upper handle assemblies shown attached to the handle sliders and handle brackets shown attached to the back wall mountable frame portion of the foldable total body imaging apparatus.
Figure 18:
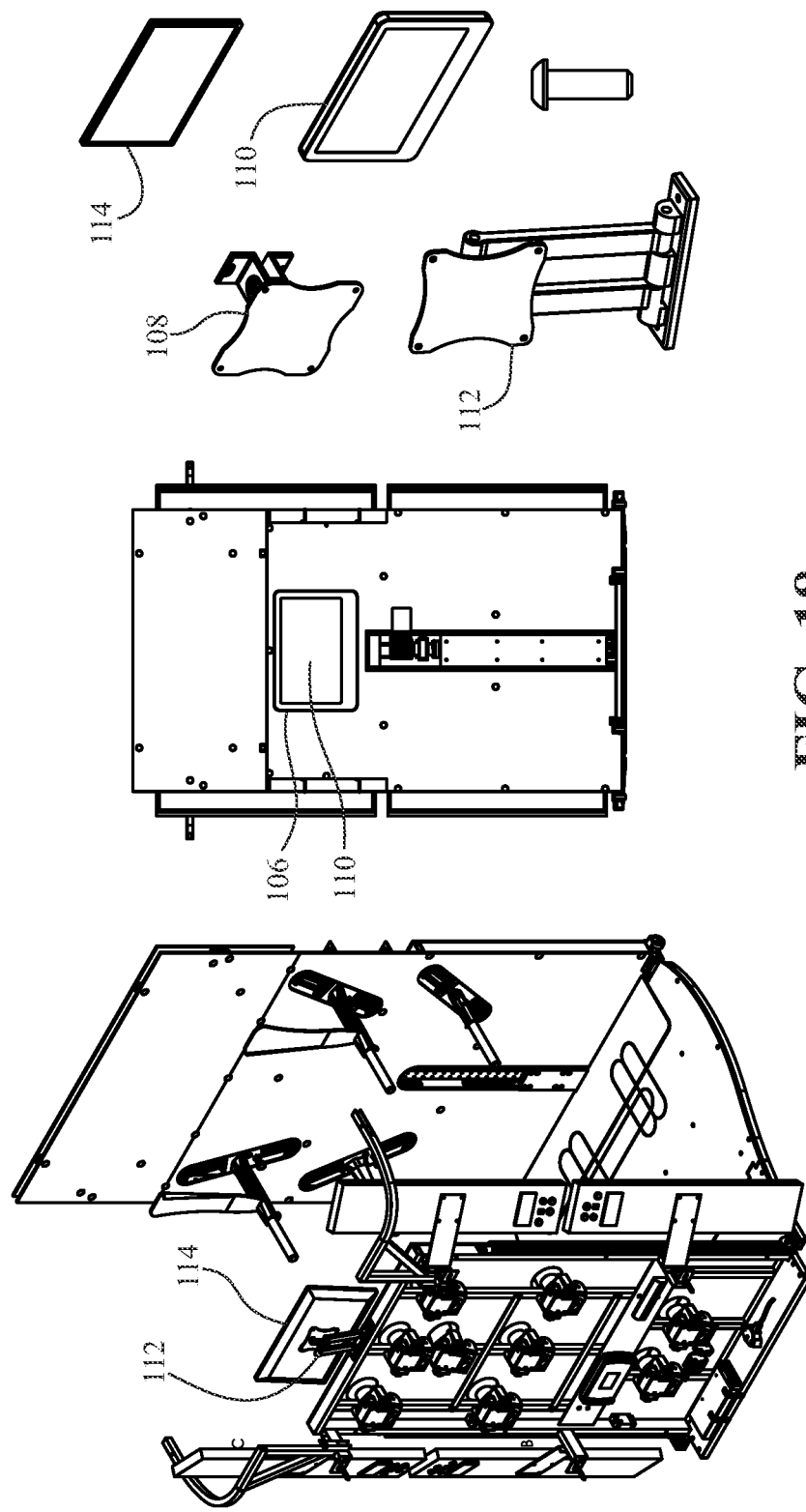
FIG. 18 is the same view as shown in FIG. 17 with the addition of the computer and patient monitor shown attached to the front frame portion of the foldable total body imaging apparatus.

The system of the present invention for patient body imaging with live feed medical consultation includes an imaging booth with a plurality of cameras for capturing body images of a patient, a server for storing and transmitting patient images and patient information, at least one computer and/or mobile computing device in communication with the server, and a computer processing unit in communication with at least one program application that includes the ability to conduct or schedule a live feed video consultation between the patient and a medical provider where the live feed video consultation enables both the patient and the medical provider to view the patient's body images. The live feed video consultation can occur immediately following the capture of a patient's body images using an image display screen contained in the imaging booth or it can take place at a later scheduled date and time where the patient and the medical provider each utilize their own computer or mobile computing device to carry out the live feed video consultation.

The system can include a program application that enables a medical provider to order and schedule the body imaging of a patient on a predesignated date and time using a predesignated imaging booth. The program application may also enable the medical provider to observe the capturing of the patient's body images in real-time via live video feed to ensure that adequate images are taken in order for the medical provider to conduct an accurate patient evaluation. The system of the present invention can also include a program application that a) delivers the patient's body images to the patient's medical provider(s) and/or medical facility in the form of an electronic medical record(s) that is/are consistent with existing electronic medical record formats and/or b) interfaces with existing electronic medical record databases to compare the patient's body images with existing medical records for the patient.

A description of an exemplary system for patient body imaging with live feed medical video consultation of the present invention and the process steps for the exemplary system are as follows:

System and Process for Asynchronous Total Body Imaging with Synchronous Live Feed Video Consultation Between Patient/User and Medical Provider 1) Patient/user and/or Medical Provider (physician, dermatologist, etc.) schedule appointment time and place for Patient/user to use Total Body Imaging Booth to take full body images of patient/user.
    ** Total Body Imaging Booths may be located in any number of locations including, but not limited to, outpatient centers, medical offices, community health centers, telehealth centers, etc.

2) Patient/user follows Total Body Imaging Booth instructions for capturing full body images of patient/user
    ** Medical provider may view taking of patient/user full body images during Imaging Booth appointment via program application to ensure adequate images and/or to determine if specific images need to be retaken during patient/user's Imaging Booth appointment
    ** Program application enables obtaining the patient/user's full body images and securely saving the patient/user's full body images to onsite server and/or servers through cloud storage where the patient/user's full body images can be later accessed by the patient/user and Medical Provider 3) Next, either A or B
    A. Patient/user has synchronous Live Feed Video Consultation with Medical provider using display screen contained within Total Body Imaging Booth immediately after taking of full body images
    ** Program application allows Patient/user and Medical Provider to view patient/user full body images together during Live Feed Video consult where Medical Provider may use personal computer, tablet, cell phone, or any other portable or non-portable electronic device capable of displaying images and live video on a display screen
    B. Synchronous Live Feed Video Consultation between patient/user and Medical Provider occurs at a later scheduled time
    ** Program application allows Patient/user and Medical Provider to later view patient/user full body images together during Live Feed Video consult where Patient/user and Medical Provider may each use personal computer, tablet, cell phone, or any other portable or non-portable electronic device capable of displaying images and live video on a display screen
    ** Live Feed Video Consult between Patient/user and Medical Provider is virtual and may occur anywhere—e.g. patient/user in patient/user's home and Medical Provider in Medical Provider's home; patient/user in patient/user's home and Medical Provider in Medical Provider's office, etc.

The imaging booth used in the system of the present invention can be foldable to create a compact device having a small footprint when the imaging booth is not in use. In one embodiment, the folding imaging booth includes a foldable floor having a locking pin for locking the foldable floor in an unfolded position for use during patient body imaging and a quick release pin for locking the foldable floor to a front frame of the front of the foldable imaging booth when the foldable floor is in a folded position. In another embodiment, the foldable imaging booth can also include a plurality of moveable and lockable curtain rails that are located between front and back frame members of the folding imaging booth and/or removable handles extending from an interior back of the foldable imaging booth for assisting the body positioning of a patient and handle holders for retaining the handles when the foldable imaging booth is in a folded position.

The present invention is also directed to a foldable total body imaging apparatus that includes a front frame member, a back frame member, a foldable floor located between the bottom of the front frame member and the bottom of the back frame member, a plurality of cameras attached to the front frame member, a plurality of movable curtain rails located between the front and back frame members, a plurality of curtain panels where at least one curtain panel is connected to each of the curtain rails to create and enclosed interior area for taking a patient's body images, a display screen connected to the front frame member, and a computer processing unit in communication with at least one program application that triggers the cameras to capture body images of a patient positioned within the enclosed interior area of the foldable total body imaging apparatus. The plurality of cameras can include a wide angle lens camera to capture a total body image of a patient and a plurality of high resolution cameras to capture different body portions of the patient. The foldable total body imaging apparatus can include body positioning members, such as a plurality of handles for the patient's hands and a footplate for the patient's feet, to assist the patient in positioning his/her body for capturing the patient's body images. The handles for the patient's hands extend from an interior back of the foldable total body imaging apparatus and are removable so that they can be retained within handle holders contained in the foldable total body imaging apparatus when the apparatus is in a folded position. This embodiment of the apparatus that includes removable handles and handle holders assists with providing a folded imaging apparatus with the smallest possible footprint.

One embodiment of the foldable total body imaging apparatus includes one or more of the following: a locking pin for locking the foldable floor in an unfolded position for use during patient body imaging, a quick release pin for locking the foldable floor to the front frame of the foldable total body imaging apparatus when the foldable floor is in a folded position, and front curtain brackets connected to the front frame member and rear curtain brackets connected to the back frame member for respectively retaining the plurality of movable curtain rails when the foldable total body imaging apparatus is in an unfolded position for patient body imaging. The plurality of curtain rails are capable of being lowered and locked into position near the back frame member and the plurality of curtain panels are capable of being secured into place on the front curtain brackets when the total body imaging apparatus is in a folded position. The foldable total body imaging apparatus of the present invention may also include a program application in communication with the computer processing unit where the program application includes the ability to conduct or schedule a live feed video consultation between the patient and a medical provider where the live feed video consultation enables both the patient and the medical provider to view the patient's body images.

FIGS. 1-6 are perspective views of a prior exemplary embodiment of a total body imaging apparatus/imaging booth and its components that can be used in accordance with the system of the present invention for patient body imaging with live feed medical video consultation. These same figures of the prior exemplary embodiment of the total body imaging apparatus that can be used with the system of the present invention can be found as FIGS. 1-6 in U.S. Pat. No. 10,702,159, which also includes a detailed description of those figures.

Figure 22:
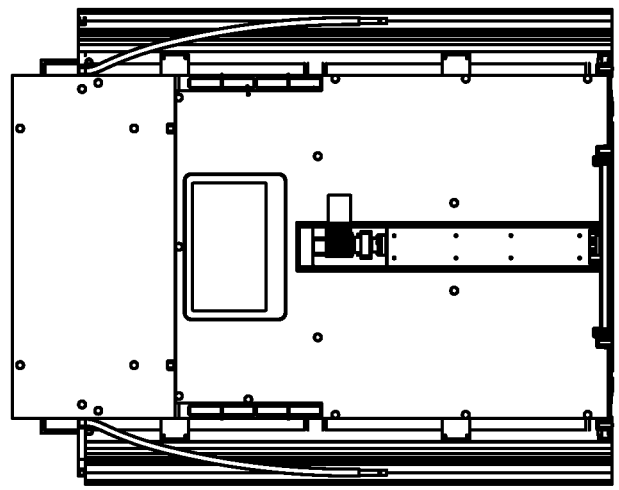
FIG. 22 is a back exterior view of the foldable total body imaging apparatus showing the operator display screen/monitor.
Figure 21:
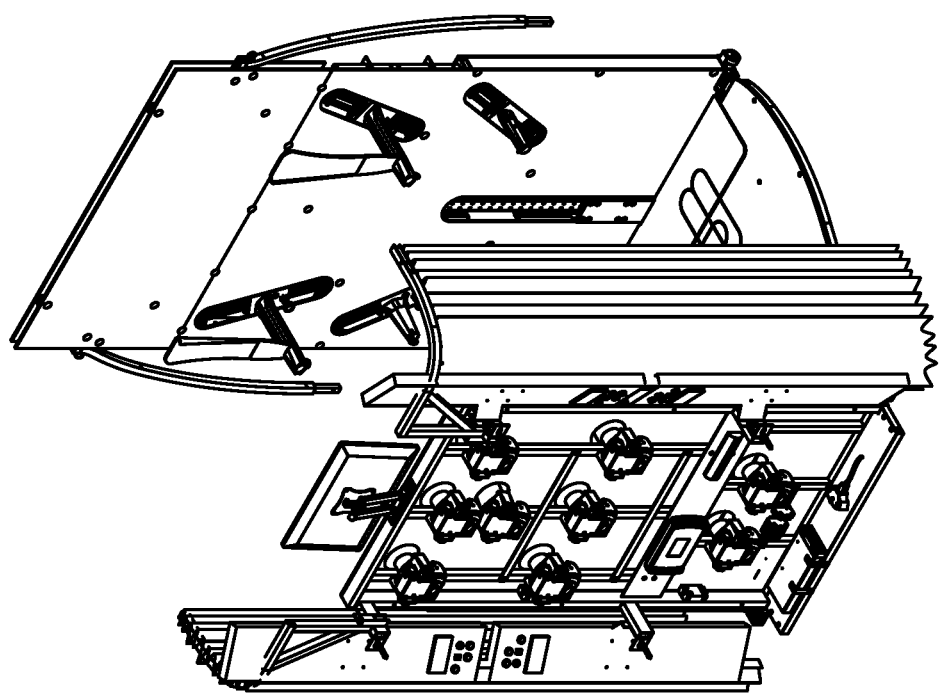
FIG. 21 is the same view as shown in FIG. 20 but with upper and lower handles shown inserted into handle holder assemblies in preparation for folding the foldable total body imaging apparatus.
Figure 24:
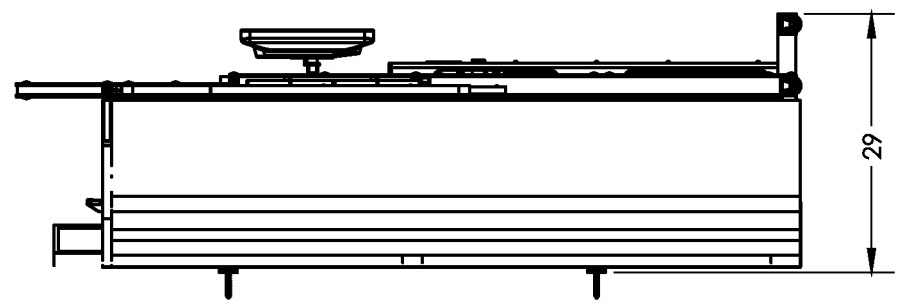
FIG. 24 is a side view of the foldable total body imaging apparatus shown in the folded up position.
Figure 23:
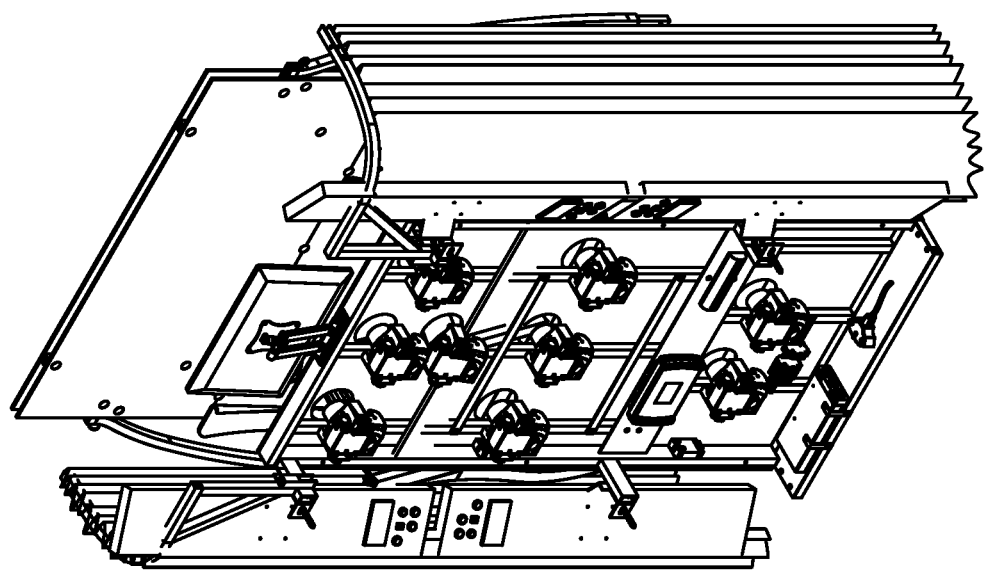
FIG. 23 is the same view as shown in FIG. 21 but with the floor plate assemblies and the bottom frame portion shown folded upwards so that the front and back frame portions are moved toward one another and then the bottom frame locked in place so that the foldable total body imaging apparatus is retained in the folded up position.
Figure 25:
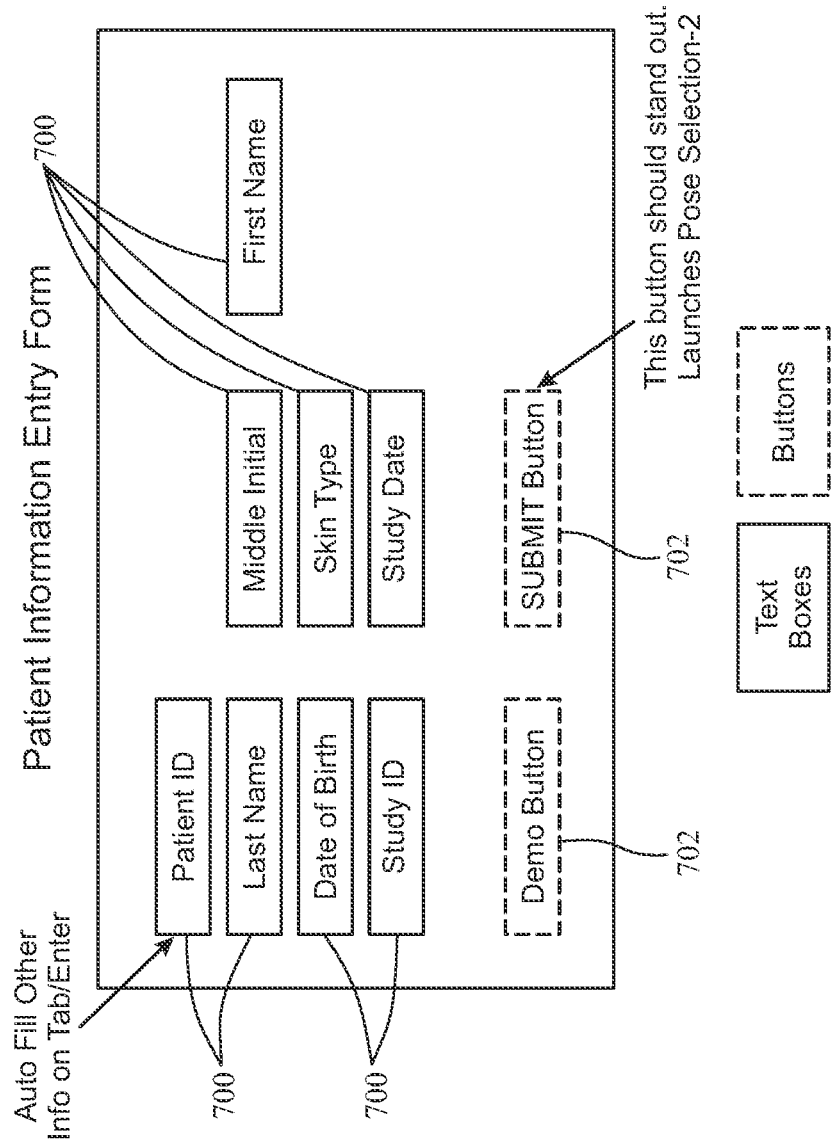
Figure 27:
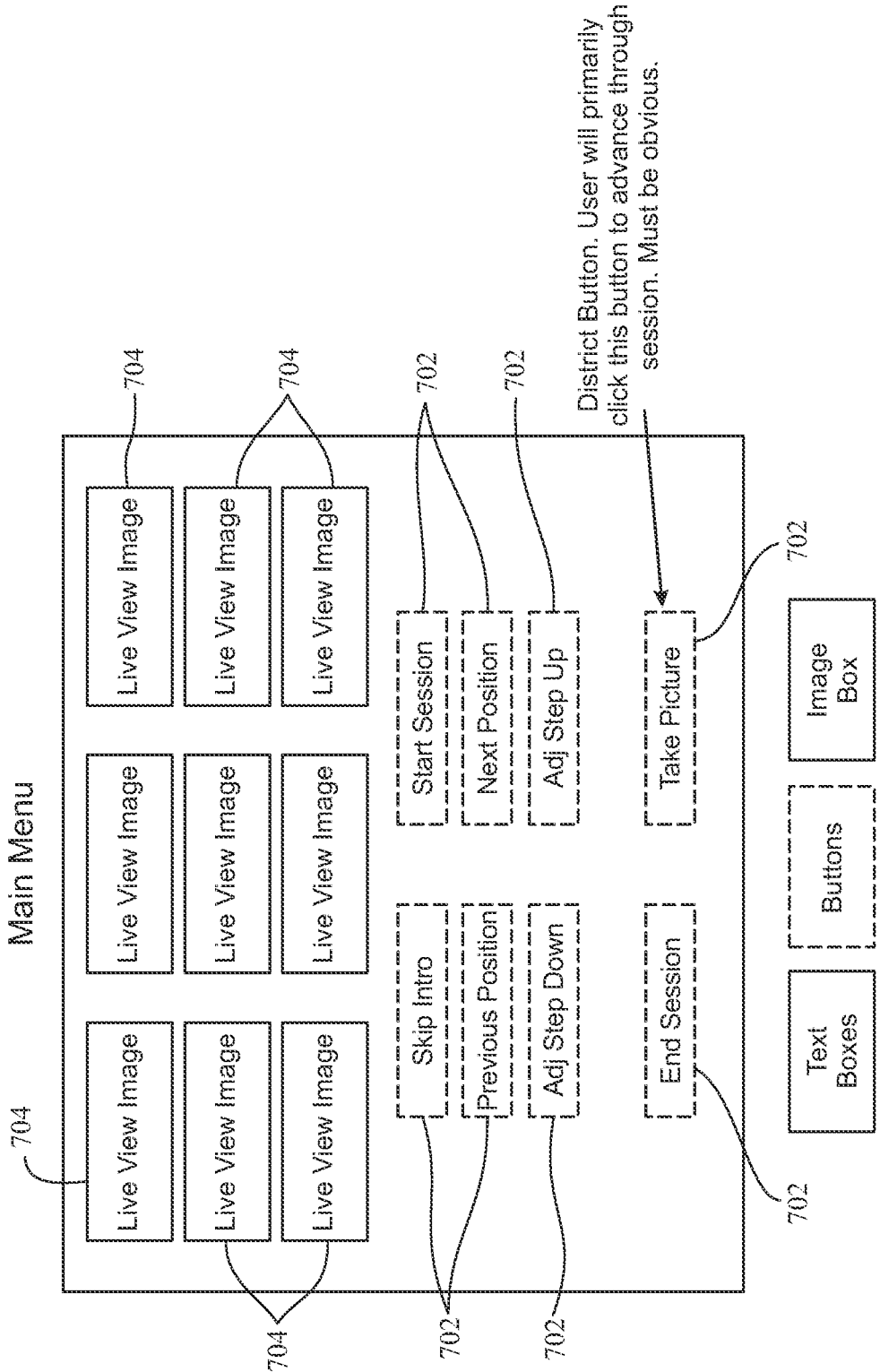
Figure 28:
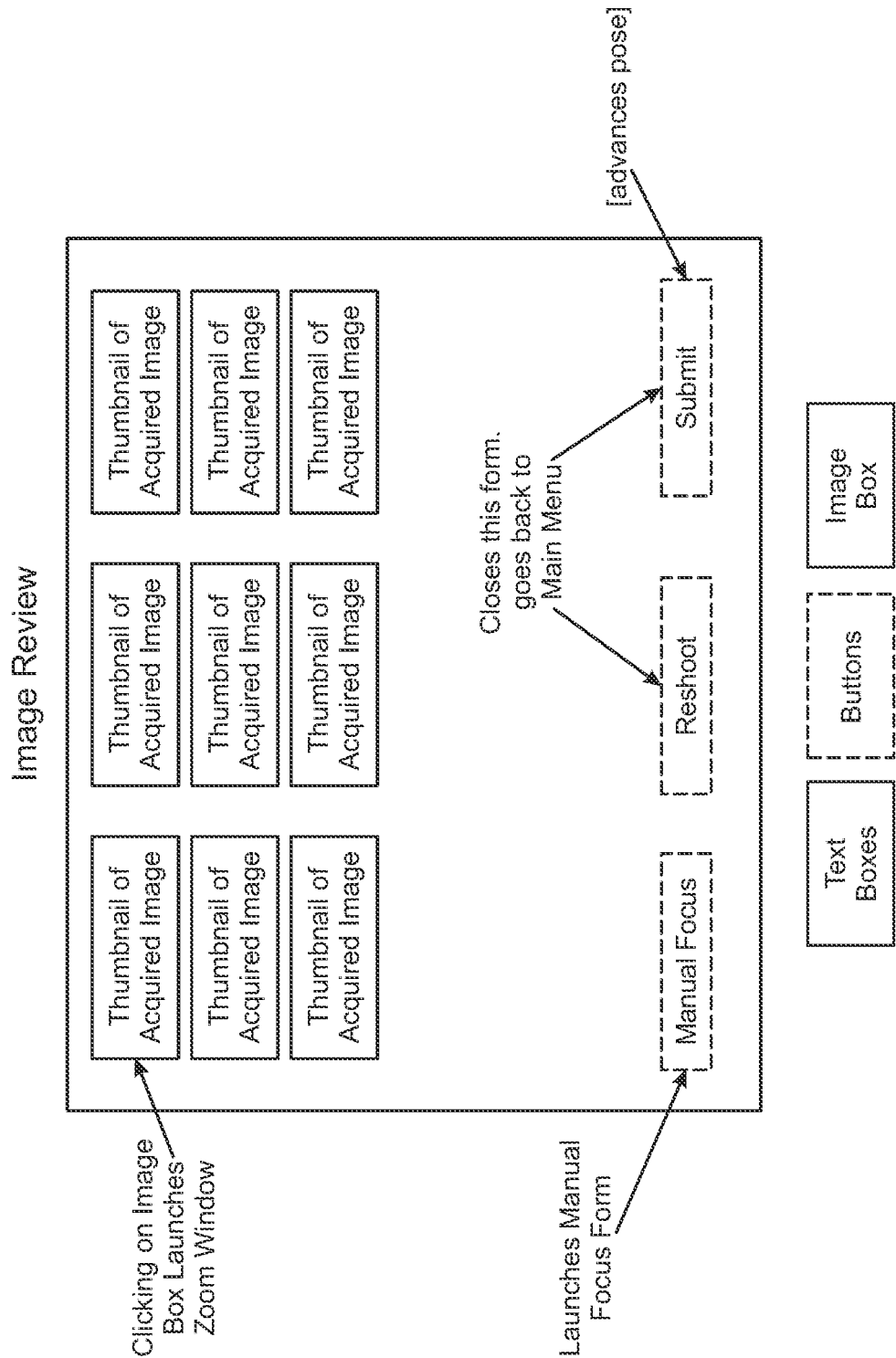
Figure 29:
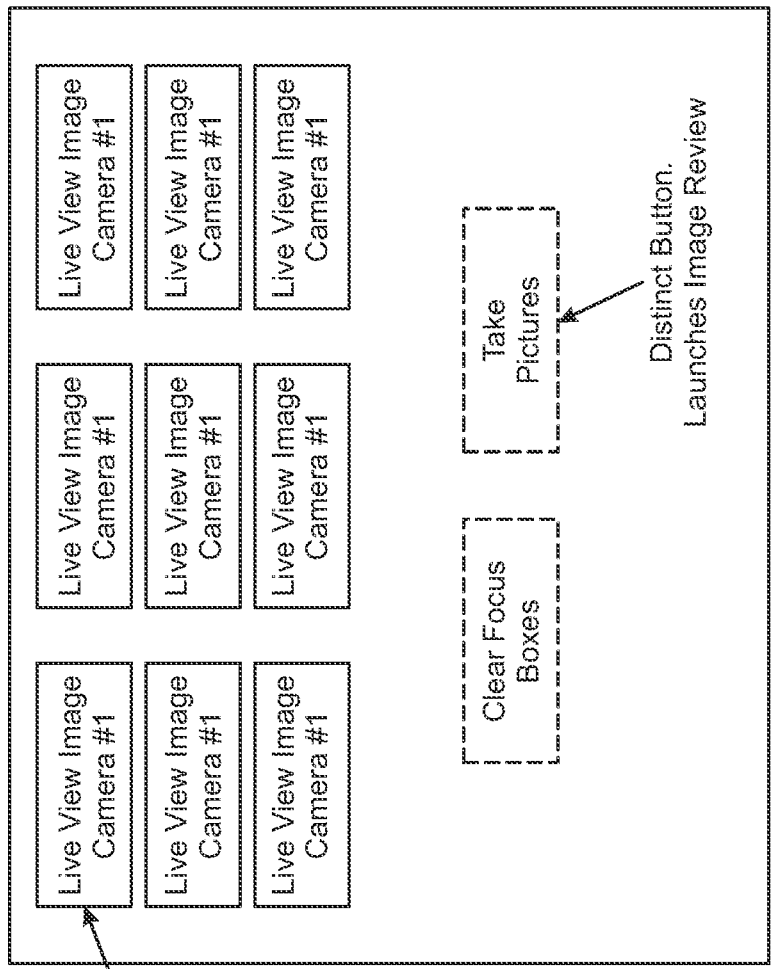
Figure 30:
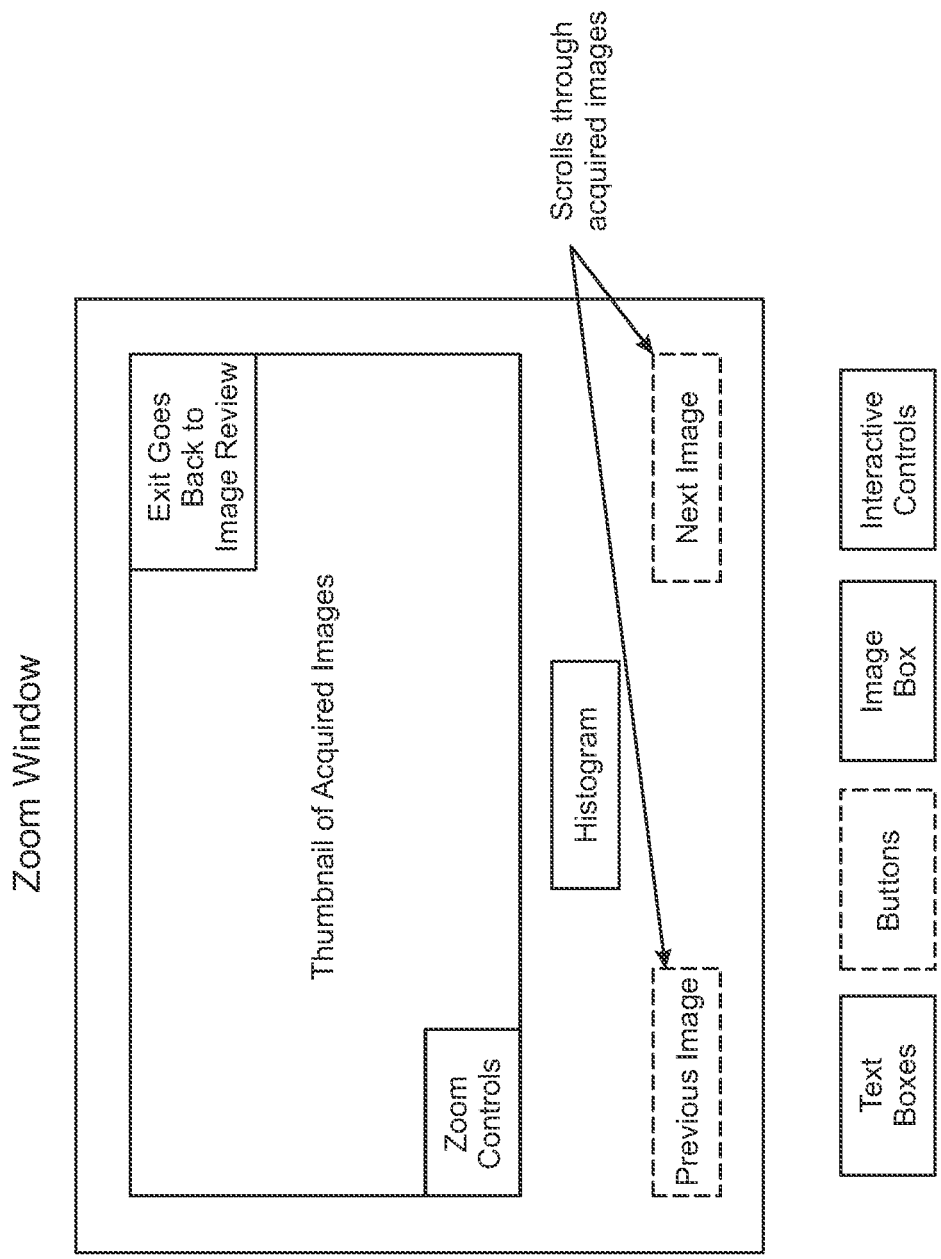
Figure 31:
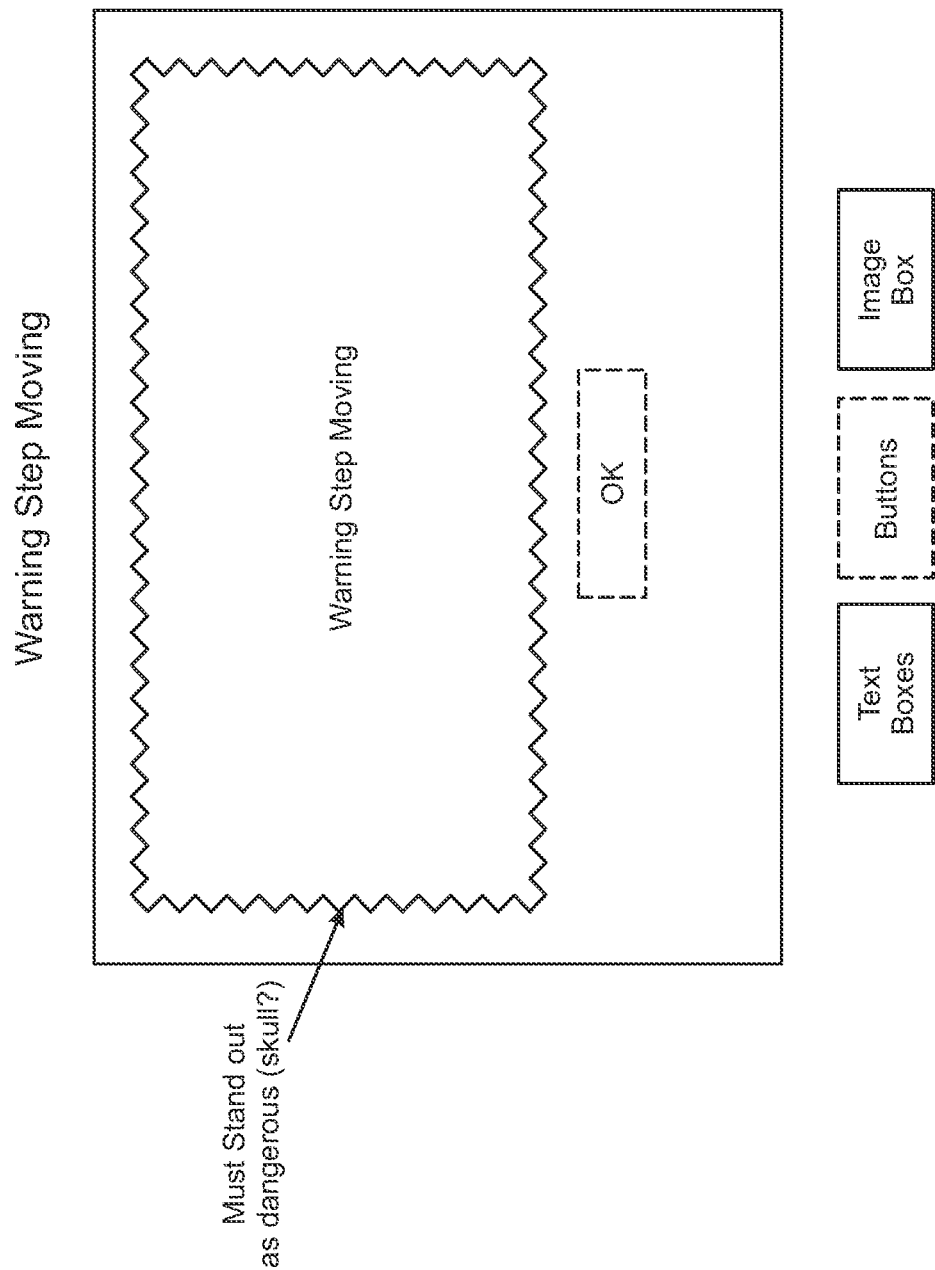
Figure 32:
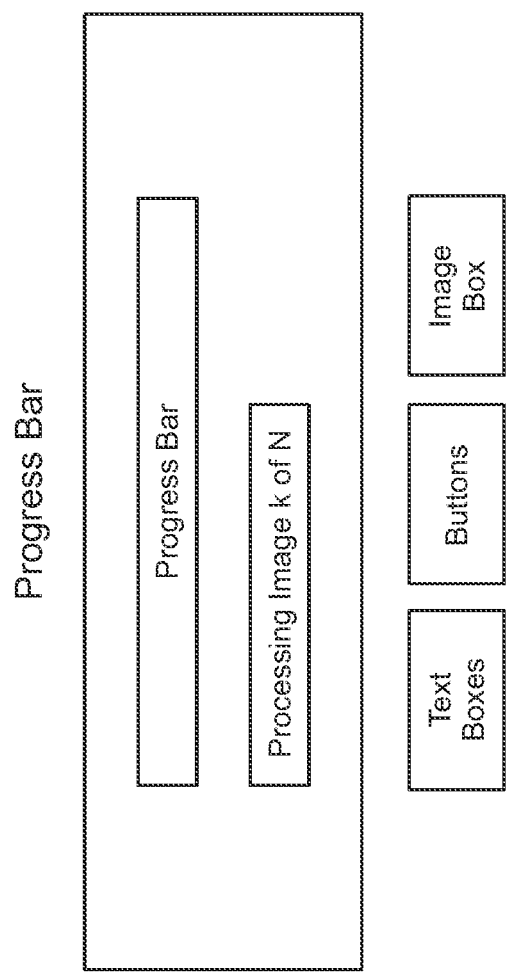
Figure 33:
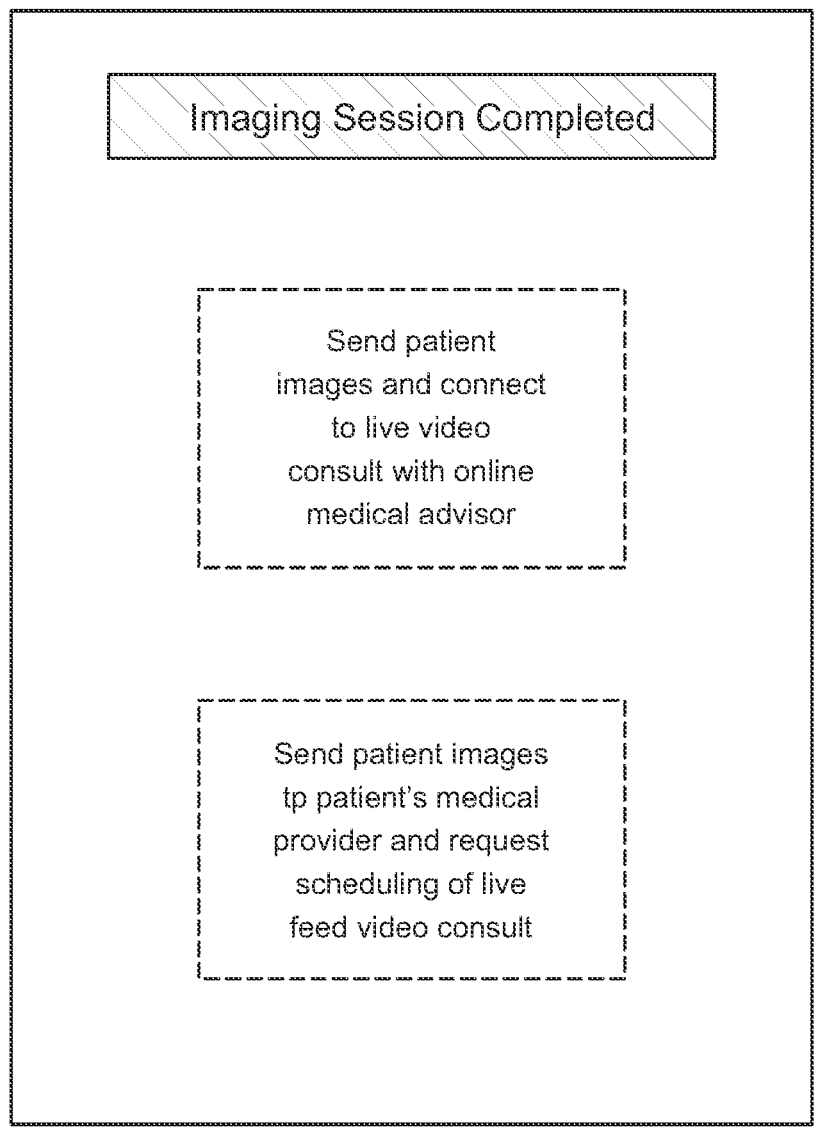

FIGS. 7-18 show perspective views of the components of an exemplary embodiment of the foldable total body imaging apparatus of the present invention as the foldable total body imaging apparatus is being constructed. FIG. 19 is a perspective view of the completed foldable total body imaging apparatus of the present invention depicted in FIGS. 7-18 shown ready to be used by a patient for patient body imaging and live feed medical video consultation. FIGS. 20-21 show perspective views of the foldable total body imaging apparatus of the present invention as it is being prepared prior to folding the floor of the apparatus to produce a compact folded apparatus for storage during non-use. FIG. 22 is a perspective view of the foldable total body imaging apparatus of the present invention shown in the folded up position.

The identity of the elements/features that relate to the numbers shown in the drawing figures are as follows:
12 back frame member
14 floor frame
16 front frame member
18 camera wall bracket
20 actuator and step assembly
22 upper back frame member
24 foldable floor assembly
30 lower right handle slider assembly
32 lower left handle slider assembly
34 upper right handle slider assembly
36 upper left handle slider assembly
38 handle holding bracket
40 wide angle lens camera
42 plurality of high resolution cameras
44 camera power supply board assembly
46 USB hub
48 triple outlet extension
50 terminal block rail assembly
52 power supply assembly
54 adapters
60 LED panels
62 brackets for LED panels
64 left front curtain bracket assembly
66 left rear curtain bracket assembly
68 right rear curtain bracket assembly
70 right front curtain bracket assembly
72 external wall cover for external back frame member
74 external wall cover for external upper back frame member
76 interior wall cover for interior back frame member
78 interior wall cover for interior upper back frame member
80 interior wall cover for front frame member having openings therethrough for cameras
92 lower right handle
94 upper right handle
96 upper left handle
98 lower left handle
100 locking pin for locking foldable floor in unfolded position
102 quick release pin for locking foldable floor to front frame member
106 computer processing unit (CPU)
108 exterior mount for exterior operator display screen/monitor
110 exterior operator display screen/monitor (note that 106 and 110 can be all-in-one CPU with display screen)
112 interior mount for patient/user display screen/monitor
114 interior patient/user display screen/monitor
120 plurality of moveable curtain rails
122 plurality of curtain panels
124 quick release pin to lock curtain panels on front curtain bracket assemblies FIGS. 25-33 show exemplary frames/screen shots of the graphic user interface for technicians/medical assistants and/or users/patients used with the foldable imaging station/booth to ensure that the automated imaging is correctly carried out and completed wherein each frame/screen shot corresponds to main windows and subsequent pop-up windows in the graphical user interface.

Figure 34:
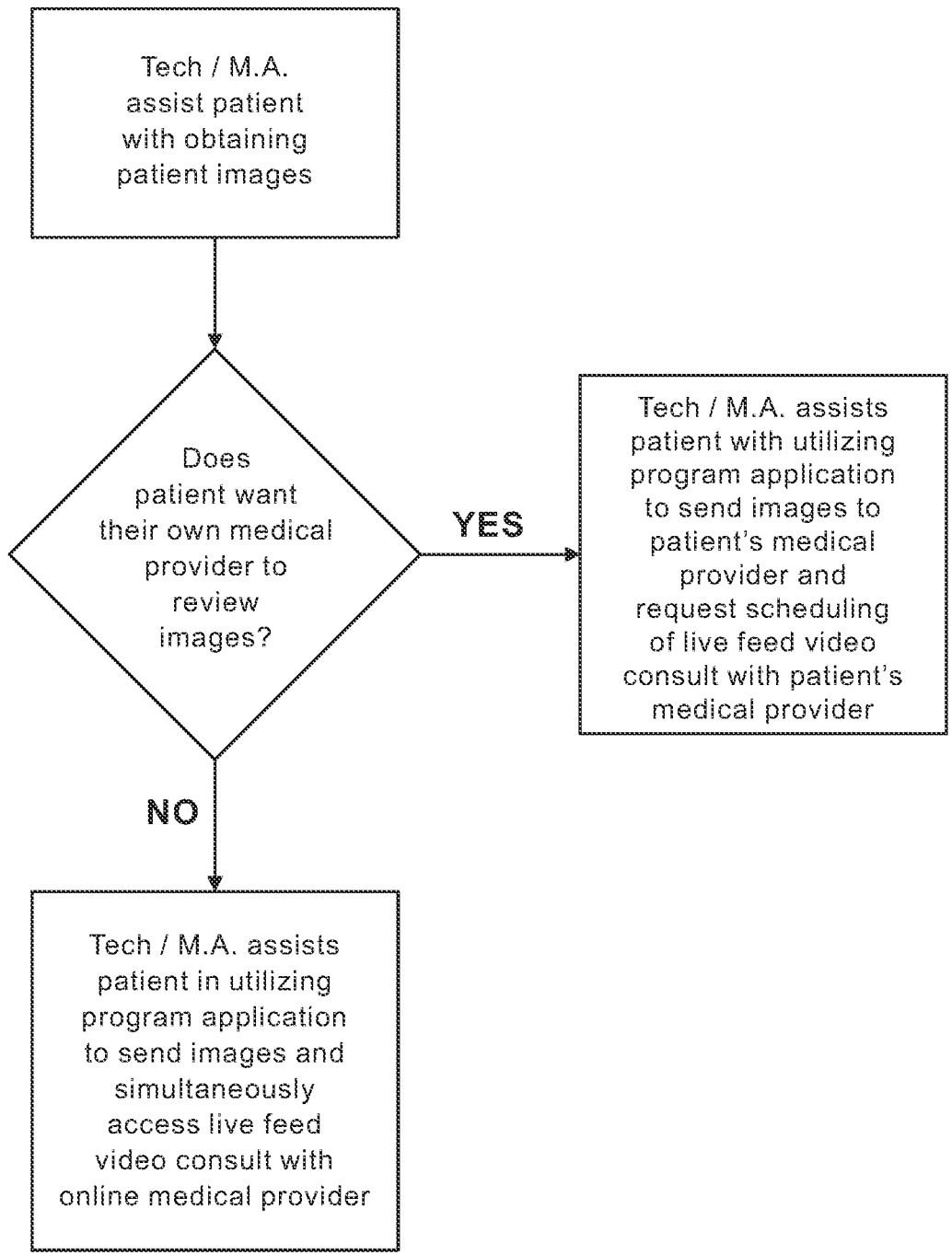
FIG. 34 is a flowchart showing the process by which a technician/medical assistant obtains and stores total body images of a user/patient and then sends the user's/patient's total body images to the user/patient's medical provider or a pre-designated online medical provider and then schedules a live feed video consultation between the user/patient and the user/patient's medical provider or the pre-designated online medical provider.

FIG. 34 is a flowchart showing the process by which a technician/medical assistant obtains and stores total body images of a user/patient and then sends the user's/patient's total body images to the user/patient's medical provider or a pre-designated online medical provider and then schedules a live feed video consultation between the user/patient and the user/patient's medical provider or the pre-designated online medical provider.

Figure 35:
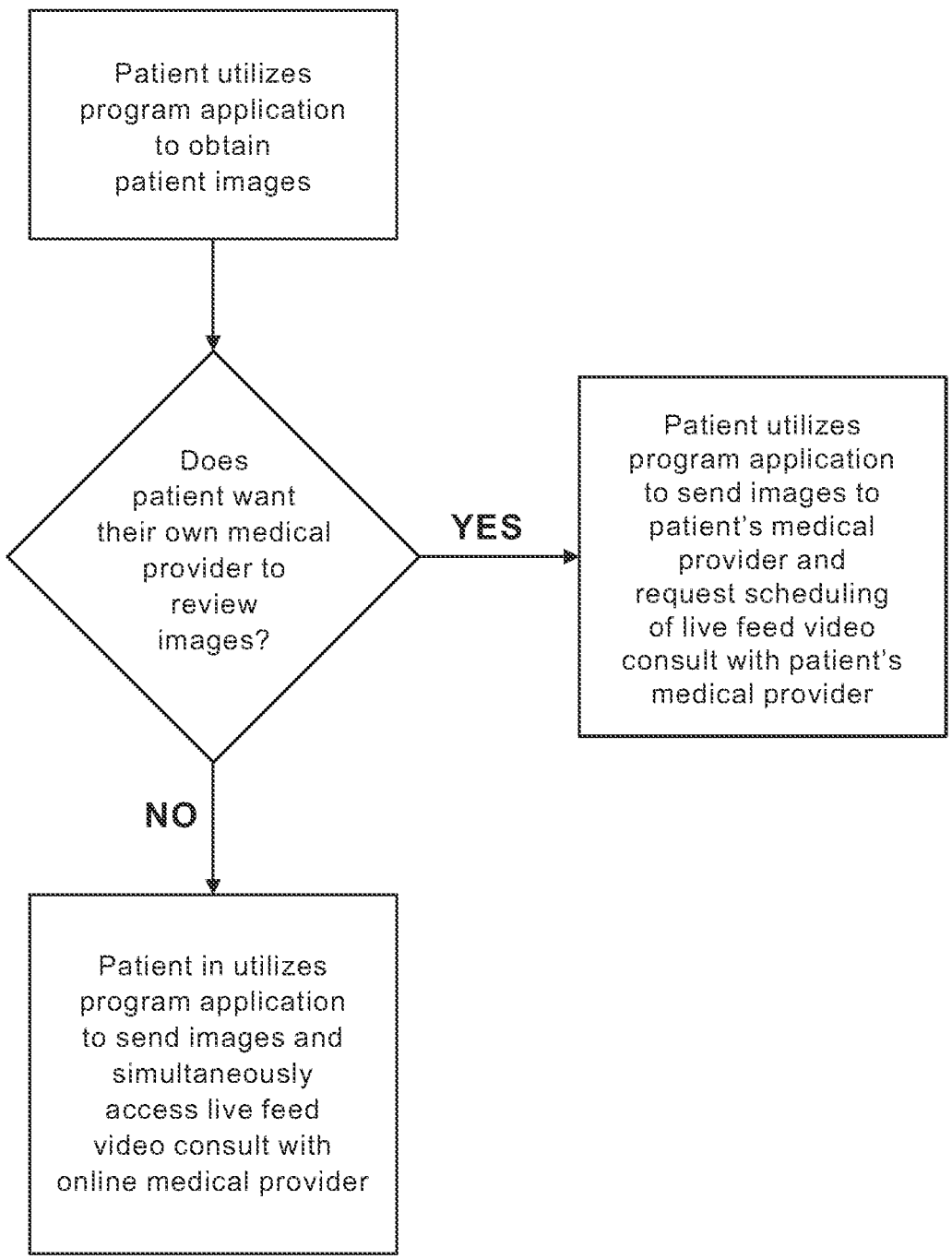
FIG. 35 is a flowchart showing the process by which a user/patient obtains and stores total body images of a user/patient and then sends the user's/patient's total body images to the user/patient's medical provider or a pre-designated online medical provider and then schedules a live feed video consultation between the user/patient and the user/patient's medical provider or the pre-designated online medical provider.
Figure 36:
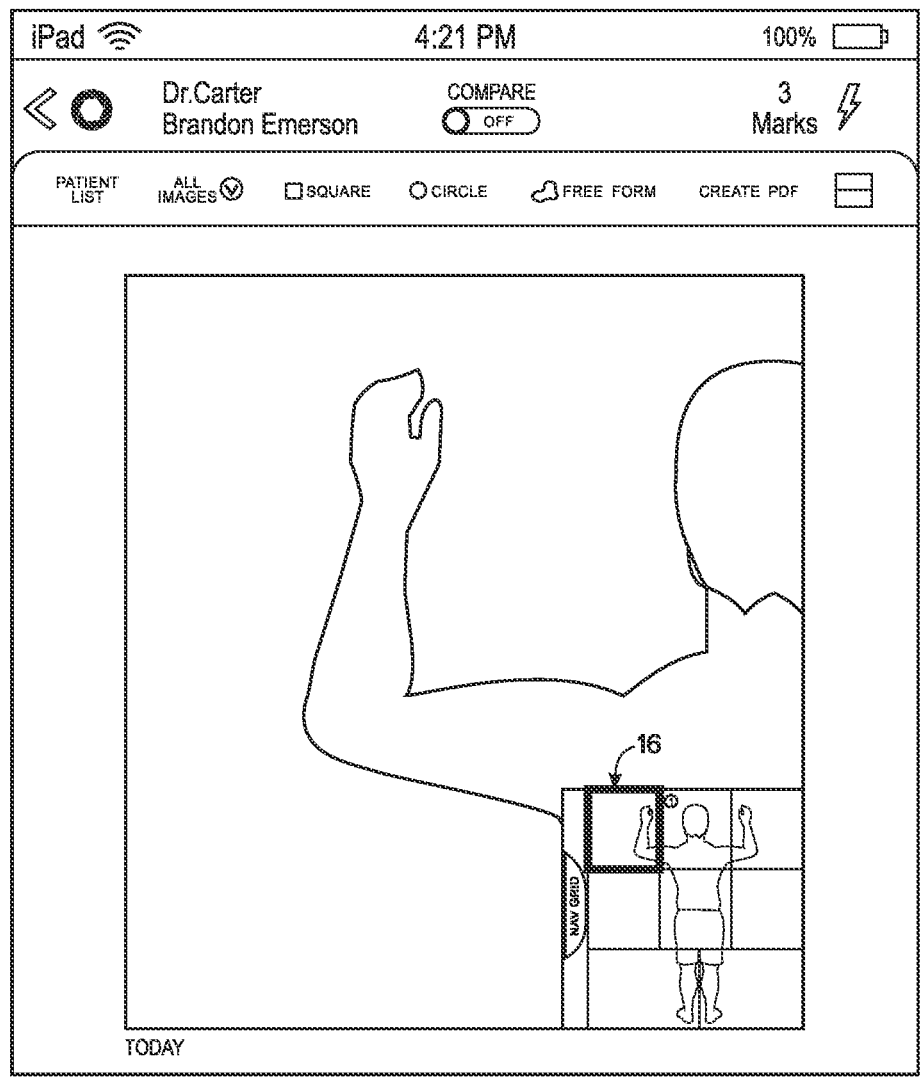
FIG. 36 is a graphical user interface (GUI) screen shot showing a reduced size image of a total body navigational grid of a user/patient that corresponds to eight high resolution camera images with the upper left tile/section of the navigational grid shown selected and the associated high resolution camera image shown magnified for more in depth viewing.
Figure 37:
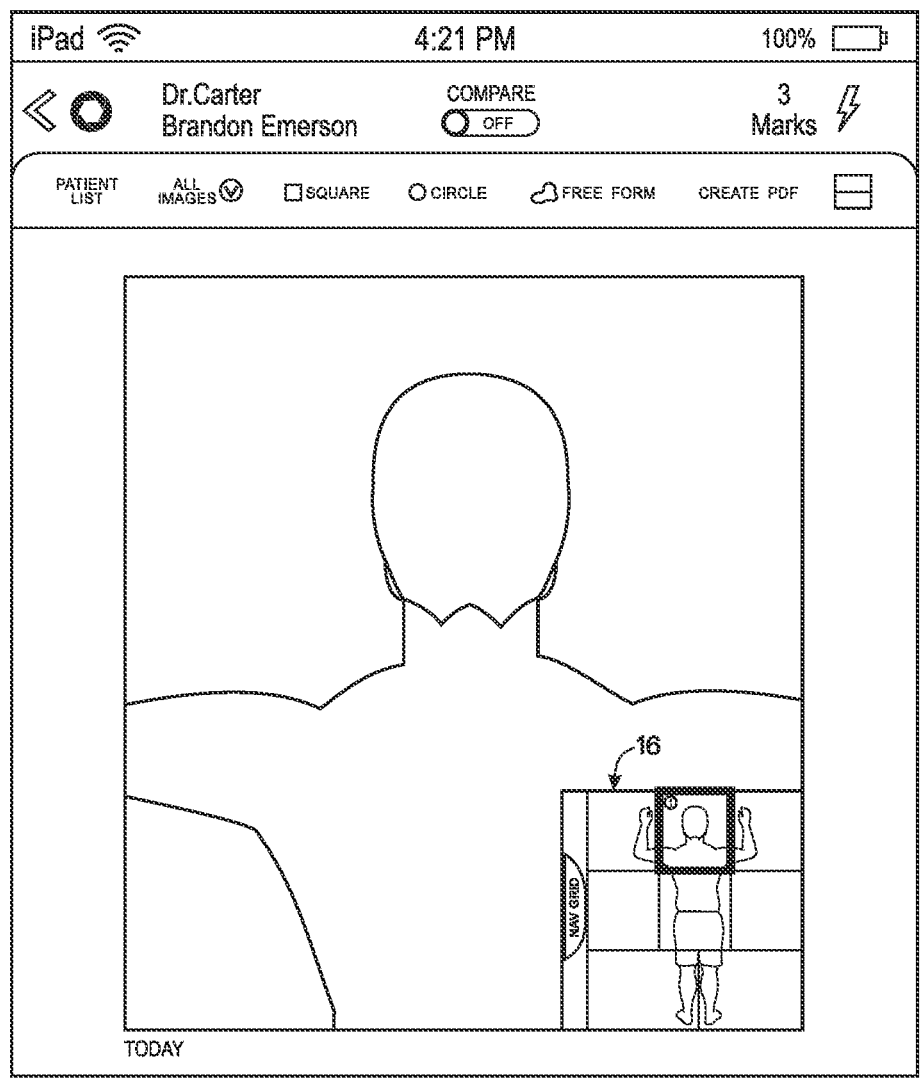
FIG. 37 is a GUI screen shot showing a reduced size image of a total body navigational grid of a user/patient that corresponds to eight high resolution camera images with the upper middle tile/section of the navigational grid shown selected and the associated high resolution camera image shown magnified for more in depth viewing.
Figure 38:
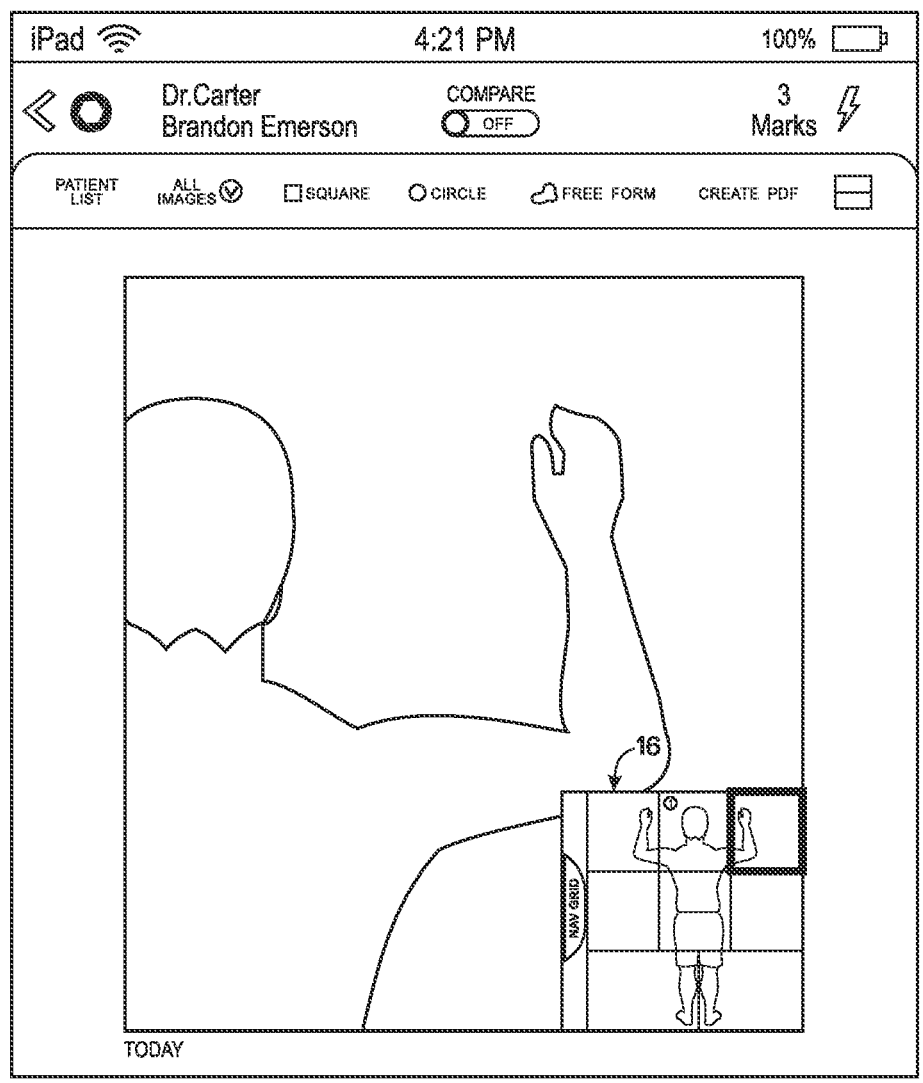
FIG. 38 is a GUI screen shot showing a reduced size image of a total body navigational grid of a user/patient that corresponds to eight high resolution camera images with the upper right tile/section of the navigational grid shown selected and the associated high resolution camera image shown magnified for more in depth viewing.
Figure 39:
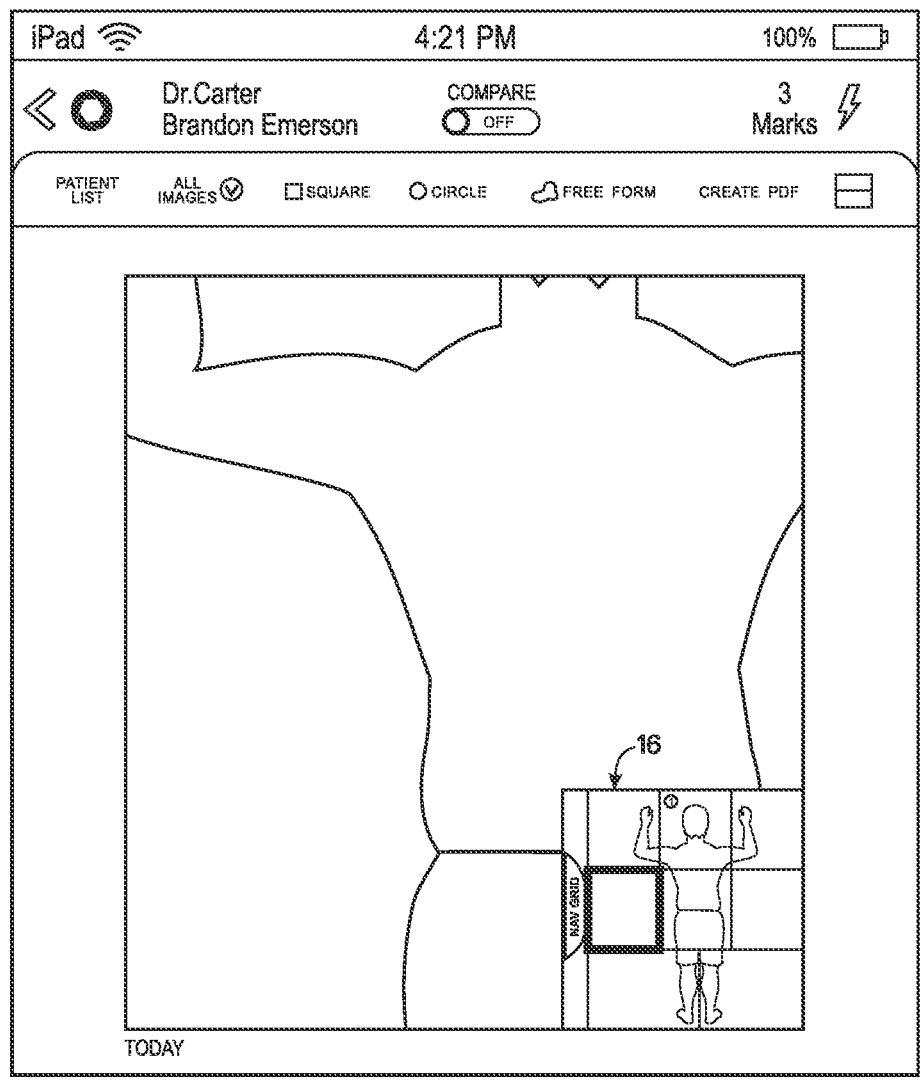
FIG. 39 is a GUI screen shot showing a reduced size image of a total body navigational grid of a user/patient that corresponds to eight high resolution camera images with the middle left tile/section of the navigational grid shown selected and the associated high resolution camera image shown magnified for more in depth viewing.
Figure 40:
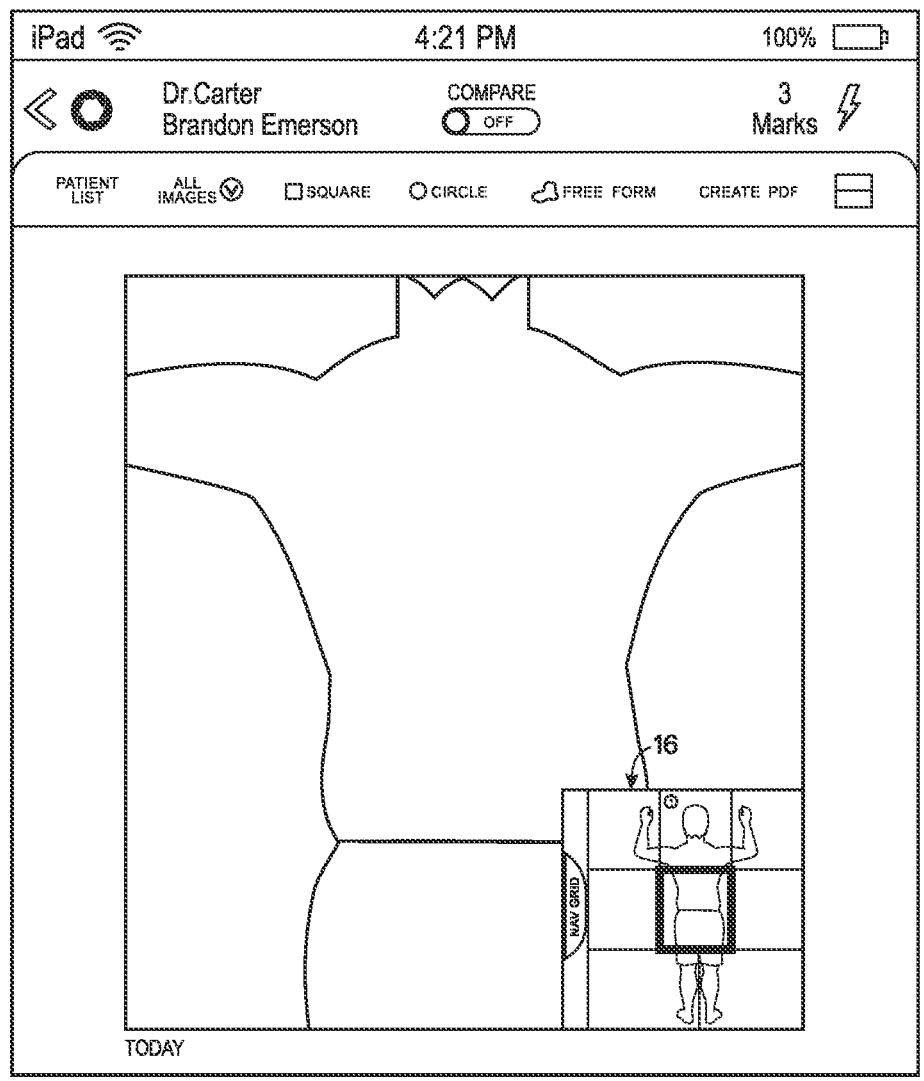
FIG. 40 is a GUI screen shot showing a reduced size image of a total body navigational grid of a user/patient that corresponds to eight high resolution camera images with the middle mid tile/section of the navigational grid shown selected and the associated high resolution camera image shown magnified for more in depth viewing.
Figure 41:
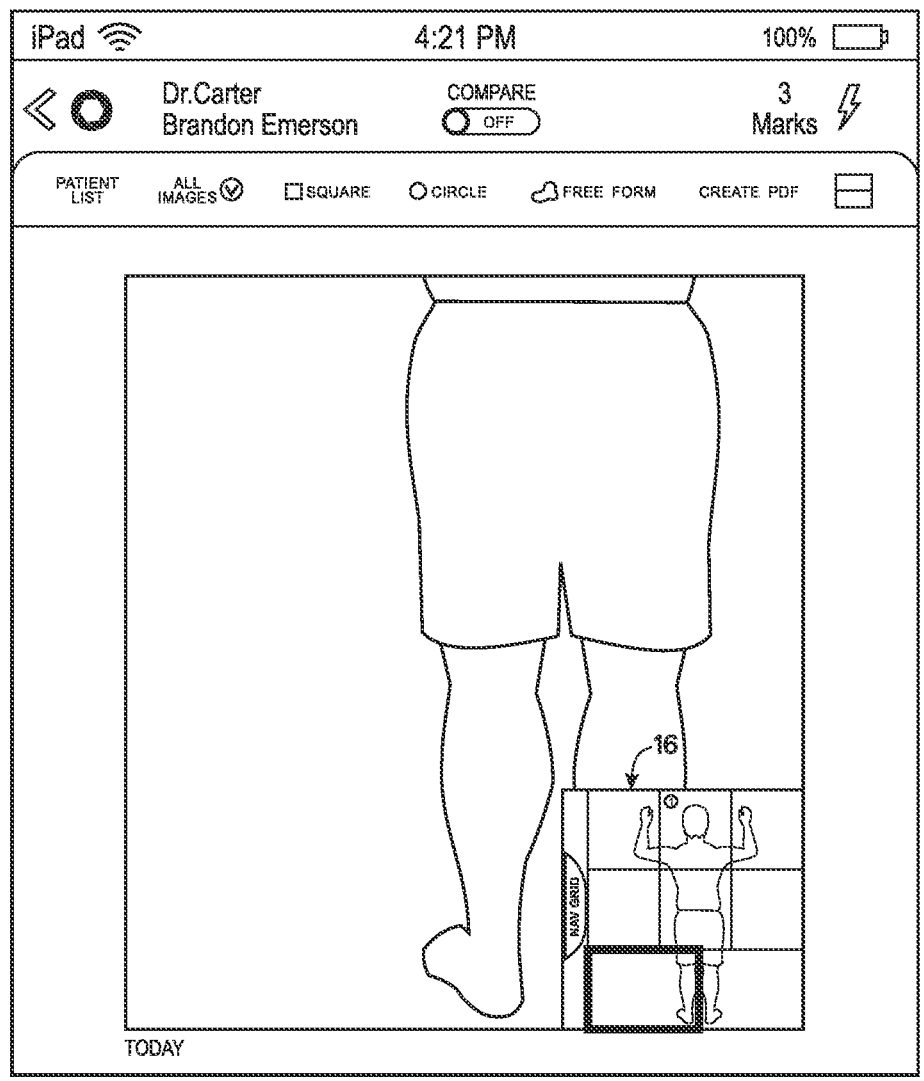
FIG. 41 is a GUI screen shot showing a reduced size image of a total body navigational grid of a user/patient that corresponds to eight high resolution camera images with the bottom left tile/section of the navigational grid shown selected and the associated high resolution camera image shown magnified for more in depth viewing.
Figure 42:
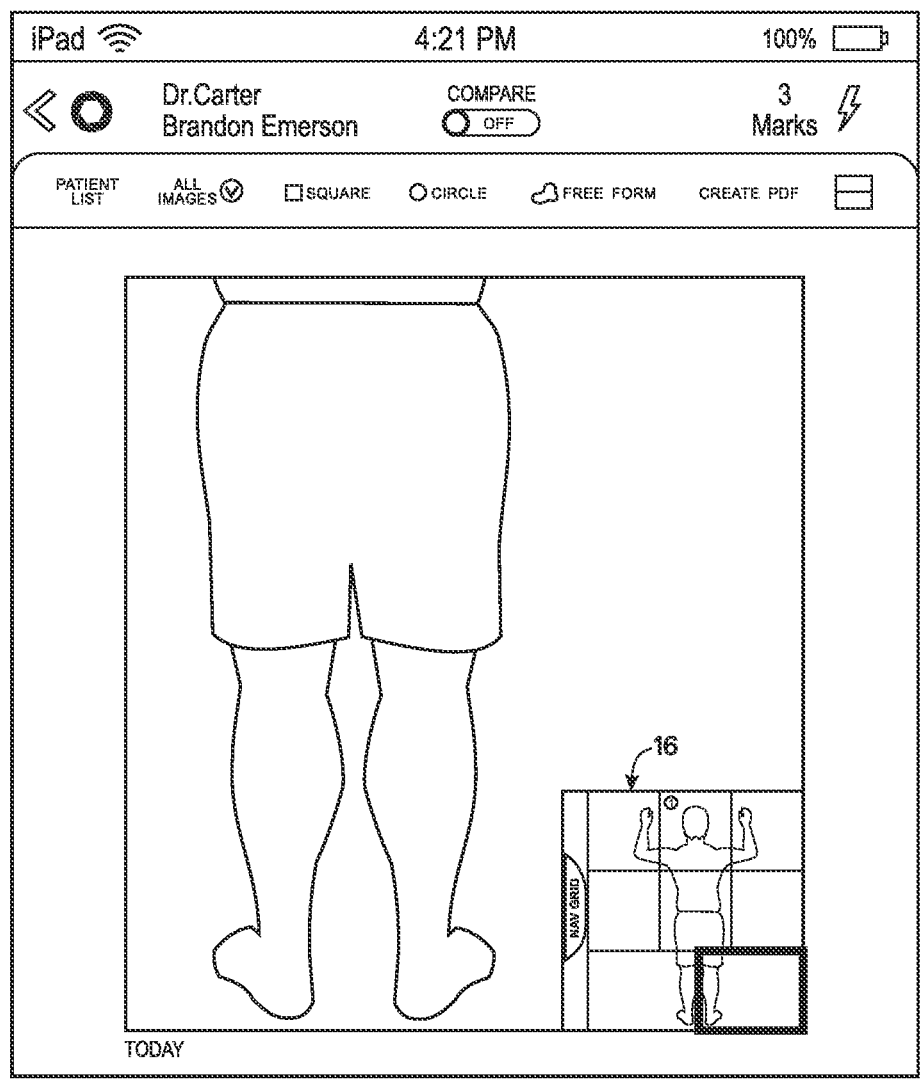
FIG. 42 is a GUI screen shot showing a reduced size image of a total body navigational grid of a user/patient that corresponds to eight high resolution camera images with the bottom right tile/section of the navigational grid shown selected and the associated high resolution camera image shown magnified for more in depth viewing.
Figure 43:
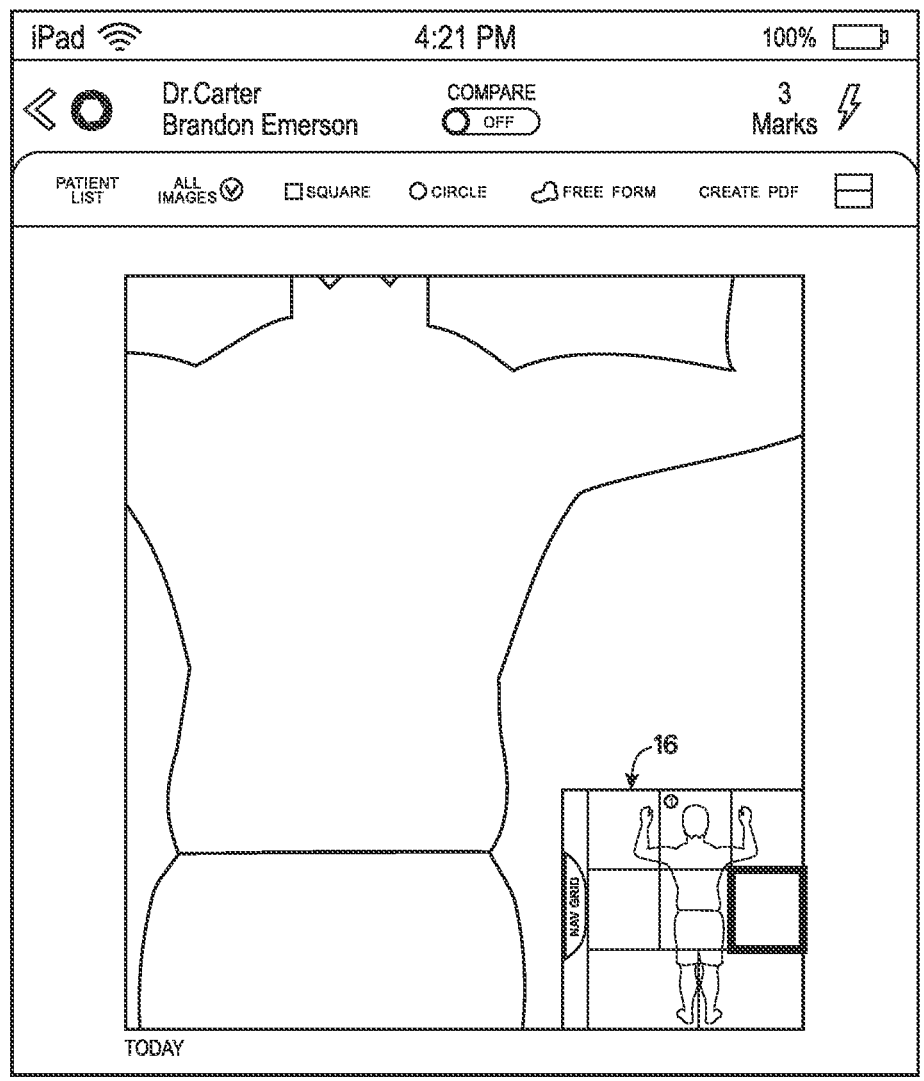
FIG. 43 is a GUI screen shot showing a reduced size image of a total body navigational grid of a user/patient that corresponds to eight high resolution camera images with the middle right tile/section of the navigational grid shown selected and the associated high resolution camera image shown magnified for more in depth viewing.

FIG. 35 is a flowchart showing the process by which a user/patient obtains and stores total body images of a user/patient and then sends the user's/patient's total body images to the user/patient's medical provider or a pre-designated online medical provider and then schedules a live feed video consultation between the user/patient and the user/patient's medical provider or the pre-designated online medical provider.

FIGS. 36-43 show exemplary graphical user (GUI) screen shots that can be used in accordance with the system of the present invention for patient body imaging with live feed medical video consultation. Each of the GUI screen shots show a reduced size image of a total body navigational grid of a user/patient that corresponds to eight high resolution camera images with a tile/section of the navigational grid shown selected and the associated high resolution camera image of the selected tile/section shown magnified for more in depth viewing. These same figures can be found as FIGS. 7-14 in U.S. Pat. No. 10,702,159, which also includes a detailed description of those figures. The exemplary GUI screen shots can be used during a live feed medical video consultation between a patient and a medical provider where the patient is able to see the same GUI screen shots as seen by the medical provider as well as the manipulations of those GYI screen shots by the medical provider and any annotations on those screen shots made by the medical provider.

The description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The following claims are included as exemplary claims only and are not intended to define or limit the scope of patentable subject matter contained within the provisional patent application.

The invention claimed is:

1. A system for patient body imaging with live feed medical video consultation comprising:
 a foldable imaging booth including a plurality of cameras for capturing body images of a patient and removable handles extending from an interior back of the foldable imaging booth for assisting body positioning of a patient and handle holders for retaining the handles when the foldable imaging booth is in a folded position;
 a server for storing and transmitting patient images and patient information;
 at least one of a computer and/or mobile computing device in communication with the server; and
 a computer processing unit in communication with at least one program application that includes the ability to conduct or schedule a live feed video consultation between the patient and a medical provider where the live feed video consultation enables both the patient and the medical provider to view the patient's body images.

2. The system of claim 1 wherein the live feed video consultation occurs immediately following the capture of the patient's body images and is performed using a display screen contained within the imaging booth.

3. The system of claim 1 wherein the live feed video consultation takes place at a later scheduled time where the patient and medical provider each utilize their own computer or mobile computing device to carry out the live feed video consultation.

4. The system of claim 1 wherein the computer processing unit is in communication with a program application that enables the medical provider to observe the capturing of the patient's body images in real-time via live feed video.

5. The system of claim 1 wherein the computer processing unit is in communication with a program application that enables the medical provider to order and schedule body imaging of the patient utilizing a predesignated imaging booth at a predesignated time.

6. The system of claim 1 wherein the computer processing unit is in communication with a program application that enables at least one of delivery of the patient's body images in the form of electronic medical records to the patient's medical provider and/or medical facility and interfacing with existing electronic medical record databases to compare the patient's body images with existing medical records for the patient.

7. The system of claim 1 wherein the foldable imaging booth includes a foldable floor having a locking pin for locking the foldable floor in an unfolded position for use during patient body imaging.

8. The system of claim 7 wherein the foldable imaging booth further includes a quick release pin for locking the foldable floor to a front frame of the foldable imaging booth when the foldable floor is in a folded position.

9. The system of claim 1 wherein the foldable imaging booth includes a plurality of movable and lockable curtain rails.

10. The system of claim 9 wherein the foldable imaging booth further includes a front frame member and a back frame member wherein the plurality of movable and lockable curtain rails are located between the front and back frame members.

11. The system of claim 10 wherein the plurality of curtain rails are each respectively connected to a front curtain bracket that is connected to the front frame member and a rear curtain bracket that is connected to the back frame member.

12. The system of claim 11 wherein the plurality of curtain rails are capable of being lowered and locked into position near the back frame member when the foldable imaging booth is in a folded position.

13. The system of claim 10 wherein the plurality of cameras are attached to the front frame member.

14. The system of claim 13 wherein the plurality of cameras include a wide angle lens camera to capture a total body image of the patient and a plurality of high resolution cameras to capture different body portions of the patient.

15. A system for patient body imaging with live feed medical video consultation comprising:
- a foldable imaging booth including a plurality of cameras for capturing body images of a patient, a foldable floor having a locking pin for locking the foldable floor in an unfolded position for use during patient body imaging, and a quick release pin for locking the foldable floor to a front frame of the foldable imaging booth when the foldable floor is in a folded position;
- a server for storing and transmitting patient images and patient information;
- at least one of a computer and/or mobile computing device in communication with the server; and
- a computer processing unit in communication with at least one program application that includes the ability to conduct or schedule a live feed video consultation between the patient and a medical provider where the live feed video consultation enables both the patient and the medical provider to view the patient's body images.

16. A system for patient body imaging with live feed medical video consultation comprising:
- a foldable imaging booth including a front frame member and a back frame member, a plurality of cameras for capturing body images of a patient connected to the front frame member, a front curtain bracket connected to the front frame member and a back curtain bracket connected to the back frame member, and a plurality of movable and lockable curtain rails located between the front and back frame members that are respectively connected to the front and back curtain brackets wherein the plurality of curtain rails are capable of being lowered and locked into position near the back frame member when the foldable imaging booth is in a folded position;
- a server for storing and transmitting patient images and patient information;
- at least one of a computer and/or mobile computing device in communication with the server; and
- a computer processing unit in communication with at least one program application that includes the ability to conduct or schedule a live feed video consultation between the patient and a medical provider where the live feed video consultation enables both the patient and the medical provider to view the patient's body images.

* * * * *